US011905555B2

(12) United States Patent
He et al.

(10) Patent No.: US 11,905,555 B2
(45) Date of Patent: Feb. 20, 2024

(54) METHODS FOR THE AMPLIFICATION OF BISULFITE-TREATED DNA

(71) Applicant: The University of Chicago, Chicago, IL (US)

(72) Inventors: Chuan He, Chicago, IL (US); Ji Nie, Chicago, IL (US); Xiao-Long Cui, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 18/057,424

(22) Filed: Nov. 21, 2022

(65) Prior Publication Data
US 2024/0011085 A1 Jan. 11, 2024

Related U.S. Application Data

(62) Division of application No. 17/250,365, filed as application No. PCT/US2019/043603 on Jul. 26, 2019, now Pat. No. 11,530,441.
(Continued)

(51) Int. Cl.
*C12Q 1/6865* (2018.01)

(52) U.S. Cl.
CPC .................. *C12Q 1/6865* (2013.01)

(58) Field of Classification Search
CPC ............ C12Q 1/6865; C12Q 2521/119; C12Q 2525/191
See application file for complete search history.

(56) References Cited

U.S. PATENT DOCUMENTS 5,399,491 A 3/1995 Kacian et al.
8,741,567 B2 6/2014 He et al.
(Continued)

FOREIGN PATENT DOCUMENTS

WO WO 2011/127136 10/2011
WO WO 2012/138973 10/2012
(Continued)

OTHER PUBLICATIONS

McGowan et al., "Promoter-Wide Hypermethylation of the Ribosomal RNA Gene Promoter in the Suicide Brain," PLoS One, May, vol. 3, issue 5, e2085, pp. 1-10 (Year: 2008).*
(Continued)

*Primary Examiner* — Young J Kim
(74) *Attorney, Agent, or Firm* — Norton Rose Fulbright US LLP

(57) ABSTRACT

The methods, compositions, and kits of the disclosure provide a novel approach for a whole genome, unbiased DNA analysis method that can be performed on limited amounts of DNA. can be used to analyze DNA to determine its modification status. Aspects of the disclosure relate to a method for amplifying bisulfite-treated deoxyribonucleic acid (DNA) molecules comprising: (a) ligating an adaptor to the DNA molecules, wherein the adaptor comprises a RNA polymerase promoter comprising bisulfite-protected cytosines; (b) treating the ligated DNA molecules with bisulfite; (c) hybridizing the bisulfite-treated DNA molecules with a primer; (d) extending the hybridized primer to make double stranded DNA; and (e) in vitro transcribing the double-stranded DNA to make RNA.

18 Claims, 20 Drawing Sheets

Specification includes a Sequence Listing.

Related U.S. Application Data

(60) Provisional application No. 62/711,184, filed on Jul. 27, 2018.

(56) References Cited

U.S. PATENT DOCUMENTS

| | | | |
|---|---|---|---|
| 2003/0104432 | A1 | 6/2003 | Xu et al. |
| 2004/0132056 | A1 | 7/2004 | Su et al. |
| 2014/0178881 | A1 | 6/2014 | Booth et al. |
| 2014/0322707 | A1 | 10/2014 | He et al. |

FOREIGN PATENT DOCUMENTS

| | | |
|---|---|---|
| WO | WO 2014/165770 | 10/2014 |
| WO | WO 2018/165459 | 9/2018 |

OTHER PUBLICATIONS

Alix-Panabières, C. & Pantel, K., "Clinical applications of circulating tumor cells and circulating tumor DNA as liquid biopsy." *Cancer discovery* 2016, 6, 479-491.

Almouzni, G. & Cedar, H., "Maintenance of Epigenetic Information" *Cold Spring Harbor perspectives in biology* 2016, 8:a019372, 23 pages.

Bettegowda et al., "Detection of Circulating Tumor Dna in Early- and Late-Stage Human Malignancies" *Sci Transl Med.* 2014, 6(224): 224ra24.

Chan et al., "Noninvasive detection of cancer-associated genome-wide hypomethylation and copy No. aberrations by plasma DNA bisulfite sequencing" *PNAS* 2013, 110, 18761-18768.

Chen et al., "Single-Cell Whole Genome Analyses by Linear Amplification via Transposon Insertion (LIANTI)" *Science* 2017, 356(6334), 189-194.

Dean et al., "Comprehensive human genome amplification using multiple displacement amplification" *PNAS* 2002, 99, 5261-5266.

Feng et al., "Disease prediction by cell-free DNA methylation" *Briefings in Bioinformatics* 2019, 20(2), 585-597.

Gawad et al., "Single-cell genome sequencing: current state of the science." *Nature Reviews Genetics* 2016, 17, 175-188.

Guo et al., "Identification of methylation haplotype blocks aids in deconvolution of heterogeneous tissue samples and tumor tissue-of-origin mapping from plasma DNA" *Nature Genetics* 2017, 49(4), 635-642.

Hodges et al., "Directional DNA Methylation Changes and Complex Intermediate States Accompany Lineage Specificity in the Adult Hematopoietic Compartment" *Mol Cell.* 2011, 44(1), 17-28.

International Search Report and Written Opinion issued in Corresponding PCT Application No. PCT/US2019/043603, dated Dec. 13, 2019.

Ito et al., "Role of Tet proteins in 5mC to 5hmC conversion, Es cell self-renewal, and ICM specification" *Nature* 2010, 466(7310), 1129-1133.

Ito et al., "Tet Proteins Can Convert 5-Methylcytosine to 5-Formylcytosine and 5-Carboxylcytosine" *Science* 2011, 333(6047), 1300-1303.

Kang et al., "CancerLocator: non-invasive cancer diagnosis and tissue-of-origin prediction using methylation profiles of cell-free DNA" *Genome Biology* 2017, 18(53), 12 pages.

Kitsera et al., "Functional impacts of 5-hydroxymethylcytosine, 5-formylcytosine, and 5-carboxycytosine at a single hemi-modified CpG dinucleotide in a gene promoter." *Nucleic Acids Res.* 2017, 45(19), 11033-11042.

Lage et al., "Whole genome analysis of genetic alterations in small Dna samples using hyperbranched strand displacement amplification and array—CGH." *Genome Research* 2003, 13, 294-307.

Lorsbach et al., "TET1, a member of a novel protein family, is fused to MLL in acute myeloid leukemia containing the t(10;11)(q22;q23)" *Leukemia* 2003, 17, 637-641.

Lun et al., "Noninvasive prenatal methylomic analysis by genomewide bisulfite sequencing of maternal plasma Dna." *Clinical Chemistry* 2013, 59(11), 1583-1594.

Motorin et al., "5-methylcytosine in RNA: detection, enzymatic formation and biological functions." *Nucleic Acids Res.* 2010, 38(5), 1415-1430.

Olova et al., "Comparison of whole-genome bisulfite sequencing library preparation strategies identifies sources of biases affecting DNA methylation data" *Genome Biology* 2018, 19(33), 19 pages.

Ono et al., "LCX, Leukemia-associated Protein with a CXXC Domain, Is Fused to MLL in Acute Myeloid Leukemia with Trilineage Dysplasia Having t(10;11)(q22;q23)[1]" *Cancer Research* 2002, 62, 4075-4080.

Schwarzenbach et al., "Cell-free nucleic acids as biomarkers in cancer patients." *Nature Reviews Cancer* 2011, 11, 426-437.

Shaw et al., "Genomic analysis of circulating cell-free DNA infers breast cancer dormancy" *Genome research* 2012, 22, 220-231.

Smallwood et al., "Single-cell genome-wide bisulfite sequencing for assessing epigenetic heterogeneity." *Nature Methods* 2014, 11(8), : 817-820.

Spits et al., "Whole-genome multiple displacement amplification from single cells" *Nature Protocols* 2006, 1(4), 1965-1971.

Sun et al., "Plasma DNA tissue mapping by genome-wide methylation sequencing for noninvasive prenatal, cancer, and transplantation assessments" *PNAS* 2015, 112, E5503-E5512.

Tahiliani et al., "Conversion of 5-Methylcytosine to 5-Hydroxymethylcytosine in Mammalian DNA by MLL Partner TET1" *Science* 2009, 324(5929), 930-935.

Wen et al., "Genome-scale detection of hypermethylated CpG islands in circulating cell-free DNA of hepatocellular carcinoma patients" *Cell Research* 2015, 25, 12501264.

Wu, Hao and Yi Zhang, "Mechanisms and functions of Tet protein-mediated 5-methylcytosine oxidation" *Genes & Development* 2011, 25, 2436-2452.

\* cited by examiner

FIG. 6B-C

METHODS FOR THE AMPLIFICATION OF BISULFITE-TREATED DNA

CROSS-REFERENCE TO RELATED APPLICATIONS

This application is a divisional of U.S. patent application Ser. No. 17/250,365 filed Jan. 11, 2021, which is a national phase application under 35 U.S.C. § 371 of International Application No. PCT/US2019/043603 filed Jul. 26, 2019, which claims the benefit of priority of U.S. Provisional Patent Application No. 62/711,184 filed Jul. 27, 2018, all of which are hereby incorporated by reference in their entirety.

STATEMENT OF GOVERNMENT SUPPORT

The invention was made with government support under grant no.: HG006827 awarded by National Institutes of Health. The government has certain rights in the invention.

SEQUENCE LISTING

The instant application contains a Sequence Listing prepared in compliance with ST.26 format and is hereby incorporated by reference in its entirety. Said Sequence Listing, created on Nov. 21, 2022, is named ARCD_P0644US_D1 Sequence_Listing.xml and is 7,300 bytes in size.

BACKGROUND OF THE INVENTION

I. Field of the Invention

Embodiments of this invention are directed generally to cell biology. In certain aspects methods involve determining whether 5-methycytosine and/or 5-hydroxymethylcytosine is present in a nucleic acid molecule.

II. Background 5-methylcytosine (5mC) and 5-hydroxymethylcytosine (5hmC) are important epigenetic markers in mammalian cells. Current 5mC and 5hmC sequencing methods can be summarized as: 1) bisulfite conversion-based methods; 2) affinity capture-based methods including antibody-based pull-down and selective chemical labeling-based pull-down; and, 3) restriction endonuclease-based methods. All these existing methods require micrograms of input genomic DNA. The large quantity of input limits the research application for rare samples and single cell systems, such as single cell behaviors during differentiation. Bisulfite conversion-based methods are considered to be the gold standard due to its ability to quantitatively differentiate 5mC and normal C in single-base resolution. However, DNA degradation is a major drawback. Affinity-based methods are relatively inexpensive but have low resolution and may lose information for low CpG density coverage (antibody-based methods). Restriction endonuclease methods have limited resolution and the coverage depends on the sequence specificity and methylation or hydroxylmethyaltion sensitivity. Overall, none of the current methods can sequence 5mC and 5hmC in small amount of DNA (nanogram scale or sub-nanogram scale) or obtain information for these modifications in single cell level. Therefore, there is a need in the art for more methods for detecting cytosine modifications such as 5mC and 5hmC in small amounts of DNA.

SUMMARY OF THE INVENTION

The methods, compositions, and kits of the disclosure provide an effective approach for a whole genome, unbiased DNA analysis method that can be performed on limited amounts of DNA and can be effective in determining the modification status of the DNA. Aspects of the disclosure relate to a method for amplifying bisulfite-treated deoxyribonucleic acid (DNA) molecules comprising: (a) ligating an adaptor to the DNA molecules, wherein the adaptor comprises a RNA polymerase promoter comprising bisulfite-protected cytosines; (b) treating the ligated DNA molecules with bisulfite; (c) hybridizing the bisulfite-treated DNA molecules with a primer; (d) extending the hybridized primer to make double stranded DNA; and (e) in vitro transcribing the double-stranded DNA to make RNA.

Aspects of the disclosure relate to a method for amplifying bisulfite-treated deoxyribonucleic acid (DNA) molecules comprising: (a) contacting the nucleic acid molecule with ligase and an adaptor under conditions suitable for ligation of the adaptor to the DNA molecule; wherein the adaptor comprises a RNA polymerase promoter comprising bisulfite-protected cytosines; (b) treating the ligated DNA molecules with bisulfite; (c) contacting the DNA molecules with a primer that is at least partially complimentary to the adaptor under conditions that allow for hybridization of the primer to the bisulfite-treated DNA molecules; (d) performing primer extension to make double stranded DNA; and (e) contacting the double stranded DNA with a RNA polymerase in the presence of NTPs under conditions suitable to in vitro transcribe the DNA to make RNA.

The term "bisulfite-protected cytosines" refers to cytosines that resist deamination after contact with bisulfite. Exemplary bisulfite-protected cytosines are described herein and include, for example, 5-methylcytosine and 5-hydroxymethylcytosine.

A further aspect of the disclosure relates to a method for identifying 5-hydroxymethylcytosine (5hmC) in a DNA molecule comprising: (1) modifying 5hmC in the DNA molecule to protect it from oxidation; (2) oxidizing the modified DNA molecule from (1) with a methylcytosine dioxygenase to convert 5-methylcytosine (5mC) to 5-carboxylcytosine (5caC); (3) performing a method comprising: (a) ligating an adaptor to the DNA molecules, wherein the adaptor comprises a RNA polymerase promoter comprising bisulfite-protected cytosines; (b) treating the ligated DNA molecules with bisulfite; (c) hybridizing the bisulfite-treated DNA molecules with a primer; (d) extending the hybridized primer to make double stranded DNA; and (e) in vitro transcribing the double-stranded DNA to make RNA. In some embodiments, step (a) is performed prior to step (1). In some embodiments, step (a) is performed after (1) and before (2). In some embodiments, (a) is performed after (2) and before (3). In some embodiments, (a) is performed after (3) and before (b).

Further aspects relate to a method for identifying 5mC in a DNA molecule comprising: (1) oxidizing the DNA molecule with an oxidant to oxidize 5hmC to 5-formylcytosine (5fC) or 5caC; (2) performing a method comprising: (a) ligating an adaptor to the DNA molecules, wherein the adaptor comprises a RNA polymerase promoter comprising bisulfite-protected cytosines; (b) treating the ligated DNA molecules with bisulfite; (c) hybridizing the bisulfite-treated DNA molecules with a primer; (d) extending the hybridized primer to make double stranded DNA; and (e) in vitro transcribing the double-stranded DNA to make RNA. In some embodiments, step (a) is performed prior to step (1).

In some embodiments, step (a) is performed after (1) and before (2). In some embodiments, (a) is performed after (2).

Yet further aspects of the disclosure relate to a method for identifying 5mC in DNA molecules comprising: (a) ligating an adaptor to the DNA molecules, wherein the adaptor comprises a RNA polymerase promoter comprising bisulfite-protected cytosines; (b) treating the ligated DNA molecules with bisulfite; (c) hybridizing the bisulfite-treated DNA molecules with a primer; (d) extending the hybridized primer to make double stranded DNA; and (e) in vitro transcribing the double-stranded DNA to make RNA; (f) reverse-transcribing the RNA to make DNA; (g) sequencing the DNA and identifying the 5mC in the sequenced DNA as a "C" in the sequence.

Further aspects of the disclosure relate to a kit comprising a DNA adaptor comprising a RNA promoter, wherein the cytosines of the RNA promoter are bisulfite-protected.

In some embodiments, the methylcytosine dioxygenase is TET1, TET2, or TET3, or a homologue thereof. In some embodiments, 5hmC is modified with a glucose or a modified glucose. In some embodiments, 5hmC is modified by a process comprising incubating the nucleic acid molecule with (3-glucosyltransferase and a glucose or modified glucose molecule. In some embodiments, the glucose molecule is a uridine diphosphoglucose molecule. In some embodiments, the modified glucose molecule is a modified uridine diphosphoglucose molecule.

In some embodiments, said oxidation selectively oxidizes 5hmC residues. In some embodiments, the oxidant is a chemical oxidizing agent. In some embodiments, the oxidant is a perruthenate oxidizing agent. In some embodiments, the oxidant comprises KRuO4. In some embodiments, the oxidant comprises an oxidant described herein.

In some embodiments, the bisulfite-protected cytosines comprise 5mC or 5hmC. In some embodiments, the bisulfite-protected cytosine comprises a oxime or hydrazone-modified In some embodiments, 5fC is modified with a compound comprising a hydroxylamine group, a hydrazine group, or a hydrazide group. In some embodiments, the compound is hydroxylamine; hydroxylamine hydrochloride; hydroxylammonium acid sulfate; hydroxylamine phosphate; O-methylhydroxylamine; O-hexylhydroxylamine; O-pentylhydroxylamine; O-benzylhydroxylamine; O-ethylhydroxylamine (EtONH$_2$), O-alkylated or O-arylated hydroxylamine, acid or salts thereof. In some embodiments, the bisulfite-protected cytosines comprise a bisulfite-protected 5caC. In some embodiments, the is an amide-modified 5caC. In some embodiments, the 5caC is amide-modified through attachment to a compound comprising an amine group. In some embodiments, the 5caC is attached to an amine group by incubating the DNA molecule with a carbodiimide derivative. In some embodiments, the compound comprising an amine group is benzylamine, substituted benzylamine, an alkylamine, an alkyldiamine, xyleneamine, substituted xyleneamine, a cycloalkylamine, a cycloalkyldiamine, hydroxylamine, or substituted hydroxylamine. In some embodiments, the bisulfite-protected cytosines comprises a 5'-alkylcytosine. The alkyl may be further substituted or unsubstituted. In some embodiments, the bisulfite-protected cytosine comprises a functional group that can change the electron density of the aromatic ring and/or increases the space hindrance to protect the cytosine from deamination.

In some embodiments, the promoter is for an RNA polymerase that is DNA-dependent. The promoter may be for a prokaryotic or non-eukaryotic RNA polymerase, such as bacteria or bacteriophage. In certain embodiments, the promoter is recognized by an RNA polymerase that is composed of a single subunit. In further embodiments, the RNA polymerase promoter comprises a SP6, T7, or T3 promoter. In some embodiments, (a) comprises end modification of the DNA and/or end repair of the DNA. In some embodiments, the end modification comprises A-Tailing. In some embodiments, (a) comprises contacting the DNA with a ligase under conditions sufficient for ligation of the adaptor to the DNA molecules. In some embodiments, the adaptor further comprises a 3' end-blocked molecule. A 3' end-blocked molecule refers to a nucleic acid that lacks the 3' phosphate that is necessary for the ligation reaction. In some embodiments, the 3' end-blocked molecule comprises a 3' phosphate as the terminal group. In some embodiments, the 3' end-blocked molecule lacks a 3' hydroxyl as the terminal group.

In some embodiments, the adaptor is partially double stranded, such as being at least or at most 20, 25, 30, 35, 40, 45, 50, 55, 60, 65, 70, 75, 80, 85, 90, 91, 92, 93, 94, 95, 96, 97, 98, 99% double stranded (or any range derivable therein). In other embodiments, there may be, be at least, or be at most 1, 2, 3, 4, 5, 6, 7, 8, 9, 10, 11, 12, 13, 14, 15, 16, 17, 18, 19, 20 or more nucleic acid residues that are single-stranded (or any range derivable therein). In some embodiments, the adaptor comprises one or more primer binding sites. In some embodiments, the adaptor comprises one or more restriction sites.

In some embodiments, (d) comprises contacting the DNA molecules with a DNA polymerase. In some embodiments, (d) comprises incubating the DNA under denaturing conditions that allow for the denaturation of double stranded DNA to single-stranded DNA. In some embodiments, (d) comprises incubating the DNA under conditions sufficient for the annealing of the primer to the single-stranded DNA. In some embodiments, (d) comprises incubating the DNA under conditions sufficient for extension of the primer to make double-stranded DNA.

In some embodiments, (e) comprises contacting the DNA molecules with an RNA polymerase and nucleoside triphosphates.

In some embodiments, the method further comprises one or more purification steps. In some embodiments, the purification step comprises solid phase reversible immobilized (SPRI) beads. In some embodiments, the method further comprises purification of the RNA molecules of (e). In some embodiments, the method further comprises isolating or purifying the nucleic acid molecules by contacting the nucleic acid molecules with a capture reagent, wherein the capture reagent binds to the affinity tag; and separating the capture reagent bound to the affinity tagged nucleic acid molecules from surrounding components.

In some embodiments, the method further comprises reverse transcription of the RNA molecules of (e) to make corresponding DNA molecules. In some embodiments, (a)-(e) are performed in order. In some embodiments, the method further comprises library construction of the corresponding DNA molecules. In some embodiments, the method further comprises sequencing the corresponding DNA molecules. In some embodiments, sequencing comprises sequencing by Sanger sequencing, Maxam-Gilbert sequencing, SOLiD sequencing, sequencing by synthesis, pyrosequencing, Ion Torrent semiconductor sequencing, massively parallel signature sequencing, polony sequencing, 454 pyrosequencing, Illumina dye sequencing, DNA nanoball sequencing, or single-molecule real-time sequencing. In some embodiments, the methods exclude bisulfite treatment of the nucleic acid.

In some embodiments, the DNA molecules are fragmented. In some embodiments, the fragments are 100-400 bp in length. In some embodiments, the fragments are 150-300 bp in length. In some embodiments, the fragments are at least, at most, or exactly 20, 30, 40, 50, 70, 80, 90, 100, 125, 150, 175, 200, 225, 250, 275, 300, 325, 350, 375 400, 425, 450, 475, 500, 525, 550, 575, 600, 625, 650, 675, 700, 725, 750, 775, 800, 825, 850, 875, 900, 950, 1000, 1050, 1100, 1150, 1200, 1300, 1400, 1500, 1600, 1700, 1800, 1900, 2000, 2100, 2200, 2300, 2400, 2500, 2600, 2700, 2800, 2900, 3000, 3200, 3400, 3600, 3800, or 4000 bp (or any derivable range therein) in length. In some embodiments, the DNA molecules comprise biological fragments, such as DNA that exists naturally in a fragmented state upon isolation. In some embodiments, the DNA molecules comprise cell-free DNA (cfDNA). In some embodiments, the cell-free DNA is isolated from serum, whole blood, plasma, or a fraction thereof. In some embodiments, the cell-free DNA is isolated from a tissue sample. In some embodiments, the fragments comprise genomic DNA. In some embodiments, the fragments comprise genomic DNA isolated from a cell. In some embodiments, the DNA molecules are fragmented and size fractionated. The size fractionation of the DNA fragments may be performed by methods known in the art such as gel fractionation, size exclusion chromatography, and through the use of commercially available kits such as EpiNext™ DNA Size Selection Kit (EpiGentek) and Select-a-Size DNA Clean & Concentrator (Zymo Research), for example.

In some embodiments, the method further comprises fragmenting the nucleic acid molecules. In some embodiments, the method further comprises tagging the nucleic acid molecules. In some embodiments, the nucleic acid is tagged and/or fragmented by a transposome. In some embodiments, tagging and/or fragmenting the nucleic acid comprises contacting the contacting the nucleic acid molecule with a transposase and a transposon. In some embodiments, the transposon comprises a P7 adapter-containing transposon. In some embodiments, the transposon comprises an affinity tag. Affinity tags can include biotin, myc, and His tags, for example.

In some embodiments, the DNA molecules used as starting material for the assay are in an amount of 1 pg-1000 ng. In some embodiments, the DNA molecules used as starting material for the assay are in an amount of 1 pg-100 ng. In some embodiments, the DNA molecules used as starting material for the assay are in an amount of 1 pg-10 ng. In some embodiments, the DNA molecules used as starting material for the assay are in an amount of 1 pg-1 ng. In some embodiments, the DNA molecules used as starting material for the assay are in an amount of 10 pg-1000 ng. In some embodiments, the DNA molecules used as starting material for the assay are in an amount of 10 pg-100 ng. In some embodiments, the DNA molecules used as starting material for the assay are in an amount of 10 pg-10 ng. In some embodiments, the DNA molecules used as starting material for the assay are in an amount of 10 pg-1 ng. In some embodiments, the DNA molecules used as the starting material for the assay are in an amount of, of at least, at most about 1, 10, 50, 100, 200, 300, 400, 500, 600, 700, 800, 900, or 1000 pg or 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 ng (or any derivable range therein).

In some embodiments, the DNA molecules are isolated from a sample from a subject. In some embodiments, the DNA molecules are isolated from a biopsy sample. In some embodiments, the sample is a liquid sample or a liquid biopsy sample. In particular embodiments, the sample is from blood, urine, cerebrospinal fluid (CSF), or aqueous humour cfDNA. In certain embodiments, a single cell is evaluated or at most 1, 2, 3, 4, 5, 6, 7, 8, 9, 10, 100, 200, 300, 400, or 500 cells (or any range derivable therein) are evaluated.

Some embodiments relate to a method for identifying biomarkers in a sample comprising DNA molecules, the method comprising performing a method of the disclosure. Some embodiments relate to a method for providing a diagnosis or prognosis for a patient comprising performing a method of the disclosure, wherein the DNA molecules are provided from a biological sample from the patient. Some embodiments relate to a method for evaluating a single cell comprising performing a method of the disclosure, wherein the DNA molecules are provided from the genomic DNA of the single cell.

In some embodiments, the method further comprises sorting a population of cells into isolated single cells. The cells may be sorted by methods known in the art such as FACS or by serial dilutions of populations of cells. In some embodiments, the method further comprises tagging the nucleic acid of each single cell with a unique nucleic acid sequence. In some embodiments, the method further comprises pooling the tagged nucleic acids into a single composition.

In some embodiments, the method further comprises end repair of the nucleic acid. End repair kits are known in the art and commercially available and can be used for the conversion of DNA containing damaged or incompatible 5' and or 3' protruding ends to 5' phosphorylated, blunt-ended DNA.

Certain methods of the disclosure are performed using a sample. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, frozen, or transported using components of a kit of the present methods. In some embodiments, the sample comprises a blood sample, a serum sample, a plasma sample, or fractions thereof. In some embodiments, the sample comprises a urine sample.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

Methods may involve any of the following steps described herein and in any particular order, unless indicated otherwise. It is specifically contemplated that any method or kit or composition discussed herein may be combined with any other embodiment discussed herein. The steps and embodiments may be utilized together in any feasible combination.

The methods of the disclosure may include 1, 2, 3, 4, 5, 6, 7, 8, 9, 10, 11, 12, 13, 14, or 15 or more of the following steps which may be performed in any order and repeated throughout any specific method embodiments: obtaining nucleic acid molecules; obtaining nucleic acid molecules from a biological sample; obtaining a biological sample containing nucleic acids from a subject; isolating nucleic acid molecules; purifying nucleic acid molecules; obtaining an array or microarray containing nucleic acids to be modified; denaturing nucleic acid molecules; shearing or cutting nucleic acid; ybridizing nucleic acid molecules; fragmenting nucleic acids; incubating the nucleic acid molecule with an enzyme; incubating the nucleic acid molecule with an enzyme that does not modify 5mC; incubating the nucleic acid molecule with a restriction enzyme; attaching one or more chemical groups or compounds to the nucleic acid or 5mC or modified 5mC; conjugating one or more chemical groups or compounds to the nucleic acid or 5mC or modified 5mC; incubating nucleic acid molecules with an enzyme that modifies the nucleic acid molecules or 5mC or modified 5mC by adding or removing one or more elements, chemical groups, or compounds; modifying or converting a 5mC to 5-hydroxymethylcytosine (5hmC); modifying 5hmC using β-glucosyltransferase (βGT); incubating β-glucosyltransferase with UDP-glucose molecules and a nucleic acid substrate under conditions to promote glycosylation of the nucleic acid with the glucose molecule (which may or may not be modified) and result in a nucleic acid that is glycosylated at one or more 5-hydroxymethylcytosines; ligating an adaptor to the DNA molecules, wherein the adaptor comprises a RNA polymerase promoter comprising bisulfite-protected cytosines; treating the ligated DNA molecules with bisulfite; hybridizing the bisulfite-treated DNA molecules with a primer; extending the hybridized primer to make double stranded DNA; and in vitro transcribing the double-stranded DNA to make RNA.

It is contemplated that some embodiments will involve steps that are done in vitro, such as by a person or a person controlling or using machinery to perform one or more steps.

Methods and compositions may involve a purified nucleic acid, modification reagent or enzyme, label, chemical modification moiety, modified UDP-G1c, and/or enzyme, such as β-glucosyltransferase. Such protocols are known to those of skill in the art.

In certain embodiments, purification may result in a molecule that is about or at least about 70, 75, 80, 85, 90, 95, 96, 97, 98, 99, 99.1, 99.2, 99.3, 99.4, 99.5, 99.6, 99.7 99.8, 99.9% or more pure, or any range derivable therein, relative to any contaminating components (w/w or w/v).

In other methods, there may be steps including, but not limited to, obtaining information (qualitative and/or quantitative) about one or more cytosine modifications in a nucleic acid sample; ordering an assay to determine, identify, and/or map cytosine modifications in a nucleic acid sample; reporting information (qualitative and/or quantitative) about one or more cytosine modifications in a nucleic acid sample; comparing that information to information about a different cytosine modification in a control or comparative sample. Unless otherwise stated, the terms "determine," "analyze," "assay," and "evaluate" in the context of a sample refer to chemical or physical transformation of that sample to gather qualitative and/or quantitative data about the sample. Moreover, the term "map" means to identify the location within a nucleic acid sequence of the particular nucleotide.

In some embodiments, nucleic acid molecules may be DNA, RNA, or a combination of both. Nucleic acids may be recombinant, genomic, or synthesized. In additional embodiments, methods involve nucleic acid molecules that are isolated and/or purified. In some embodiments, the nucleic acid molecules are fragmented. In some embodiments, the nucleic acid molecules are natural fragments. Natural fragments refers to nucleic acid molecules that exist in nature as fragments, such as cell-free DNA and fetal DNA, by way of example. The nucleic acid may be isolated from a cell or biological sample in some embodiments. Certain embodiments involve isolating nucleic acids from a eukaryotic, mammalian, or human cell. In some cases, they are isolated from non-nucleic acids. In some embodiments, the nucleic acid molecule is eukaryotic; in some cases, the nucleic acid is mammalian, which may be human. This means the nucleic acid molecule is isolated from a human cell and/or has a sequence that identifies it as human. In particular embodiments, it is contemplated that the nucleic acid molecule is not a prokaryotic nucleic acid, such as a bacterial nucleic acid molecule. In additional embodiments, isolated nucleic acid molecules are on an array. In particular cases, the array is a microarray. In some cases, a nucleic acid is isolated by any technique known to those of skill in the art, including, but not limited to, using a gel, column, matrix or filter to isolate the nucleic acids. In some embodiments, the gel is a polyacrylamide or agarose gel.

Methods and compositions may also involve one or more enzymes. In some embodiments, the enzyme is a polymerase. In certain cases, embodiments involve a restriction enzyme. The restriction enzyme may be methylation-insensitive. It is contemplated that a step for achieving a result with an enzyme involves incubating the enzyme under reaction conditions to achieve that result. Such conditions include, but are not limited to, temperature, pressure, pH, viscosity, volume, and the presence of any cofactors for the reaction, which are known by those of skill in the art. It may include one of more reaction buffers. In some embodiments, a reaction can be stopped by heat inactivation, dilution, pH change, or addition of a compound that interferes with the reaction or by alteration of a condition that halts the reaction.

Methods and compositions involve detecting, characterizing, and/or distinguishing between cytosine modifications. Methods may involve identifying 5mC in the nucleic acids by comparing modified nucleic acids with unmodified nucleic acids or to nucleic acids whose modification state is already known. Detection of the modification can involve a wide variety of recombinant nucleic acid techniques. In some embodiments, a modified nucleic acid molecule is incubated with polymerase, at least one primer, and one or more nucleotides under conditions to allow polymerization of the modified nucleic acid. In additional embodiments, methods may involve sequencing a modified nucleic acid molecule. In other embodiments, a modified nucleic acid is used in a primer extension assay.

Methods and compositions may involve a control nucleic acid. The control may be used to evaluate whether modification or other enzymatic or chemical reactions are occurring. Alternatively, the control may be used to compare modification states. The control may be a negative control or it may be a positive control. It may be a control that was not incubated with one or more reagents in the modification reaction. Alternatively, a control nucleic acid may be a reference nucleic acid, which means its modification state (based on qualitative and/or quantitative information related to modification at 5mCs, or the absence thereof) is used for comparing to a nucleic acid being evaluated. In some embodiments, multiple nucleic acids from different sources provide the basis for a control nucleic acid. Moreover, in some cases, the control nucleic acid is from a normal sample with respect to a particular attribute, such as a disease or condition, or other phenotype. In some embodiments, the control comprises non-cancerous tissues. In some embodiments, the control comprises a cut-off value. In some embodiments, the control sample is from a different patient population, a different cell type or organ type, a different disease state, a different phase or severity of a disease state, a different prognosis, a different developmental stage, etc.

Embodiments also concern kits, which may be in a suitable container, that can be used to achieve the described methods. Embodiments of the disclosure relate to a kit comprising a DNA adaptor comprising a RNA promoter, wherein the cytosines of the RNA promoter are bisulfite-protected. In some embodiments, the kit comprises a ligase and/or ligase buffer. In some embodiments, the kit comprises bisulfite. In some embodiments, the kit further comprises a primer that is complementary to the adaptor. In some embodiments, the kit further comprises dNTPs. In some embodiments, the kit further comprises a DNA polymerase. In some embodiments, the kit further comprises nuclease-free water. In some embodiments, the kit further comprises a protease. In some embodiments, the kit further comprises a RNA polymerase. In some embodiments, the kit further comprises NTPs. In some embodiments, the kit further comprises an oxidant. In some embodiments the kit further comprises a dioxygenase. In some embodiments, the kit further comprises a compound comprising a hydroxylamine group, a hydrazine group, or a hydrazide group. In some embodiments, the kit further comprises a compound comprising an amine group. In some embodiments, the kit further comprises a 3' end-blocked molecule. In some embodiments, the kit further comprises SPRI beads. In some embodiments, the kit further comprises reverse transcriptase. In some embodiments, the kit further comprises glucose or modified glucose. In some embodiments, the kit further comprises β-glucosyltransferase.

In certain aspect, the contents of a kit can include a methylcytosine dioxygenase, or its homologue and a 5-hydroxymethylcytosine modifying agent. In further aspects, the methylcytosine dioxygenase is TET1, TET2, or TET3. In other embodiments the kit includes the catalytic domain of TET1, TET2, or TET3. In certain aspects, the 5hmC modifying agent, which refers to an agent that is capable of modifying 5hmC, is β-glucosyltransferase.

In additional embodiments, a kit also contains a 5hmC modification, such as uridine diphophoglucose or a modified uridine diphophoglucose molecule. In particular embodiments, the modified uridine diphosphoglucose molecule can be uridine diphospho6-$N_3$-glucose molecule. In additional embodiments, a kit may also contain biotin.

Certain embodiments are directed to kits comprising a vector comprising a promoter operably linked to a nucleic acid segment encoding a methylcytosine dioxygenase or a portion and a 5-hydroxymethylcytosine modifying agent. In certain aspects, the nucleic segment encodes TET1, TET2, or TET3, or their catalytic domain. In certain aspects, the 5hmC modifying agent is β-glucosyltransferase. In additional aspects, a kit also contains a 5hmC modification, such as uridine diphophoglucose or a modified uridine diphophoglucose molecule. In particular embodiments, the modified uridine diphosphoglucose molecule can be uridine diphospho6-$N_3$-glucose molecule. In additional embodiments, a kit may also contain biotin.

In some embodiments, there are kits comprising one or more modification agents (enzymatic or chemical) and one or more modification moieties. The molecules may have or involve different types of modifications. In further embodiments, a kit may include one or more buffers, such as buffers for nucleic acids or for reactions involving nucleic acids. Other enzymes may be included in kits in addition to or instead of β-glucosyltransferase. In some embodiments, an enzyme is a polymerase. Kits may also include nucleotides for use with the polymerase. In some cases, a restriction enzyme is included in addition to or instead of a polymerase. In some embodiments, the kits include a nucleic acid probe. The nucleic acid probe may or may not already be modified. In some embodiments, the kits include modification moieties for attaching to the nucleic acid probe.

Other embodiments also concern an array or microarray containing nucleic acid molecules that have been modified at the nucleotides that were 5hmC and/or 5mC. In some embodiments, the microarray comprises fragmented nucleic acids isolated from a sample.

The following patent applications describe embodiments useful in the methods of the current disclosure: WO2011127136, WO2012138973, and WO2014165770, which are herein incorporated by reference.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention. In addition, any step recited in the context of one method may be employed (as a substituting step or as an added step) in the context of any other method disclosed herein. Any method may omit one or more steps as recited herein.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed herein with the term"comprising" or "comprises" may be substituted with the phrase "consisting of" or "consisting essentially of," as these terms are understood in the context of patent law.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 6A-C. (A) Percentage contributions of different tissues to plasma cfDNA for 6 healthy individuals and 6 CRC patients. Each bar means the proportion of each individual. (B) The contributions of colon in CRC patients' and Healthy individuals' plasma. (C) The contributions of neutrophils in CRC patients' and Healthy individuals' plasma.

DETAILED DESCRIPTION

Figure 1A:
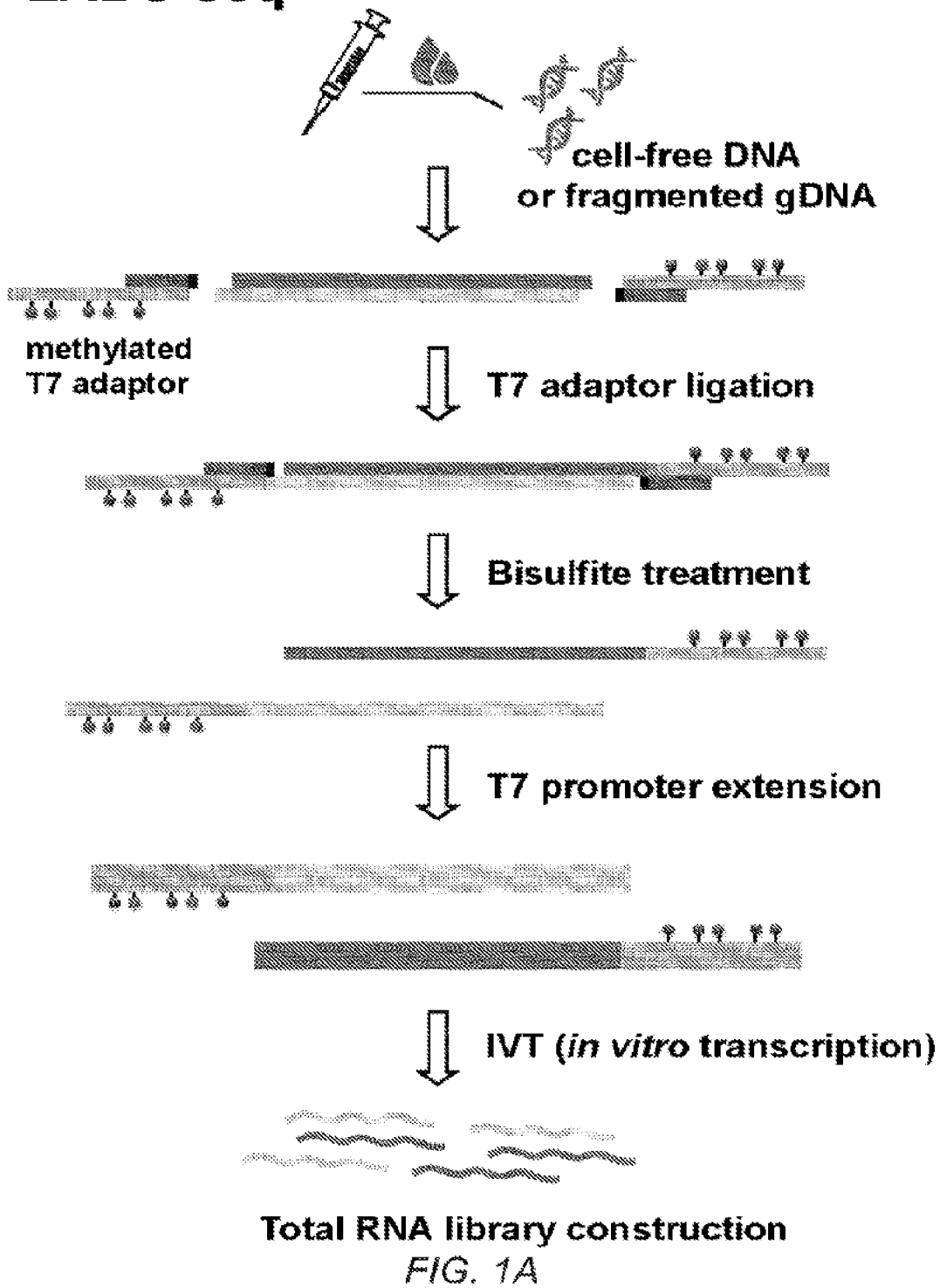
FIGS. 1A-E. (A) Workflow of LAB S-seq: cell-free DNA or fragmented genomic DNA are ligated with fully methylated T7 adaptors; perform bisulfite treatment and T7 promoter extension; IVT amplification followed by total RNA library preparation and sequencing. (B) Mapping efficiency, global CpG methylation level and duplication level for LABS-seq libraries constructed by 10 pg, 20 pg, 50 µg, 100 pg, 1 ng, 10 ng and 100 ng (with technical replicates). Each point is a library. (C) Chromosome coverage comparison among LAB S-seq, MethylC-seq and EpiGnome. (D) Genome browser view of DNA methylation profiles. (E) Scatter plots showing correlation between LAB S-seq to bulk reference and LAB S-seq replicates with Pearson correlation (r) displayed.

The genome-wide sequencing of 5-methylcytosine (5mC) at single base resolution from samples with limited DNA material, such as liquid biopsy samples, for example (down to sub-nanogram) remains challenging because of strategy difficulties, bisulfite degradation and low library complexity. This disclosure relates to a method termed Linear Amplification based whole genome Bisulfite Sequencing method (LAB S-seq), with which tiny amount of cell-free DNA materials can be evenly and linearly amplified by in vitro transcription without loss or bias of methylome information. The method displayed high genome coverages, along with low duplication level and high mapping ratio. Presenting high quality data especially at sub-nanogram level, LABS-seq enables to explore DNA modification dynamic changes and differential methylation signatures of cell-free DNA liquid biopsy for tumor markers identification and tissue-of-origin prediction.

I. MOLECULAR BIOLOGY METHODS

The methods of the current disclosure include certain molecular biology applications that are known and well-described in the art. For example, methods of the current disclosure include ligation of an adaptor to the DNA molecules. A typical ligase reaction can include a DNA ligase (eg. T4 DNA ligase), a ligase buffer, the pieces of DNA to be joined by the ligation reaction, and a diluent, such as water or nuclease-free water. Ligases include ligases from *E. coli*, T4 DNA ligase from bacteriophage T4, mammalian ligases, and thermostable ligases (eg. Ampligase DNA ligase) and variants and modified forms thereof. After the components of the ligation reaction are prepared and mixed, the reaction is typically performed by incubating the components at conditions suitable for activity of the ligase. In some embodiments, these conditions may include a temperature of about 16° C. and a time of about 2 or more hours. In some embodiments, the time may be reduced by using high concentration T4 DNA ligase. In some embodiments, the reaction is then exposed to heat (eg. 65° C.) to inactivate the enzyme.

In some embodiments, the methods include library construction of a nucleic acid molecules. The term "library" refers to a collection (e.g., to a plurality) of vehicles that comprise the nucleic acid molecules. The vehicle may be a vector, construct, array, or other physical vehicle. A "vector" or "construct" (sometimes referred to as gene delivery or gene transfer "vehicle") refers to a macromolecule, complex of molecules, or viral particle, comprising a polynucleotide to be delivered to a host cell, either in vitro or in vivo. The polynucleotide can be a linear or a circular molecule. One of skill in the art would be well equipped to construct a vector through standard recombinant techniques (see, for example, Maniatis et al., 1988 and Ausubel et al., 1994, both incorporated herein by reference). An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,789,162, 5,708,153, 6,040,193 and 5,800,992, which are hereby incorporated in their entirety for all purposes. The vehicle may comprise restriction endonuclease sites that may be used for further cloning or other molecular biology procedures. The vehicle may also comprise primer binding sites that can be used for sequencing, for PCR amplification, and/or for quantitative PCR studies.

In some embodiments, the nucleic acids are purified. Purification of nucleic acids may be performed in between any of the steps described herein. In some embodiments, the purification of nucleic acids excludes column filtration. In some embodiments, purification comprises phenol chloroform, magnetic beads, a silica based method (eg. silica membrane in the presence of chaotropic salts), and anion exchange. In some embodiments, the purification comprises SPRI (Solid Phase Reversible Immobilization) beads. SPRI beads are paramagnetic (magnetic only in a magnetic field) and this prevents them from clumping and falling out of solution. Each bead is made of polystyrene surrounded by a layer of magnetite, which is coated with carboxyl molecules. It is these that reversibly bind DNA in the presence of the "crowding agent" polyethylene glycol (PEG) and salt (20% PEG, 2.5M NaCl is the magic mix). PEG causes the negatively-charged DNA to bind with the carboxyl groups on the bead surface. As the immobilization is dependent on the concentration of PEG and salt in the reaction, the volumetric ratio of beads to DNA is critical. SPRI is particularly suitable for low concentration DNA cleanup.

Some embodiments of the disclosure relate to primer extension. Primer extension refers to annealing a primer to a DNA (referred to as the template, since it serves as a template for the production of a new strand) and adding a polymerase and dNTPs and inclubating the reaction under conditions that allow for the production of a DNA moleuclde that extends in the 5'-3' direction from the primer. The annealing of the primer is typically achieved by incubating single-stranded DNA with a primer under conditions suitable for binding of the primer to the single-stranded DNA. The primer should be at least partially complementary to allow binding. In some embodiments, the primer may have a non-complementary region that allows for the addition of sequences not in the template DNA. The primer may have a region that is 100, 99, 98, 97, 96, 95, 94, 93, 92, 91, 90, 89, 88, 87, 86, or 85% complementary to the template DNA (or any range derivable therein). This region is capable of annealing to the template DNA. The annealing step can be done at a temperature that allows for the binding of the template DNA to the primer. This is typically about 3-5° C. below the Tm of the primer. Once the primer is annealed, the annealed primer and template DNA can be incubated with dNTPs (NTPs if reaction is for making RNA) and a polymerase under conditions suitable for the production of a nucleic acid through the extension of the primer. A typical polymerase used is taq (*Thermus aquaticus*) polymerase. The temperature of the extension reaction depends on the temperature that the polymerase exhibits activity at. For taq, a typically extension temperature is approximately 70-80° C.

In some embodiments, PCR amplification may be performed of DNA molecules of the methods of the disclosure. A basic PCR set-up requires several components and reagents, including: a DNA template that contains the DNA target region to amplify, a DNA polymerase, an enzyme that polymerizes new DNA strands; heat-resistant Taq polymerase is especially common, as it is more likely to remain intact during the high-temperature DNA denaturation process; one or more DNA primers that are complementary to the 3' (three prime) ends of each of the sense and anti-sense strands of the DNA target; deoxynucleoside triphosphates, or dNTPs (sometimes called "deoxynucleotide triphosphates"; nucleotides containing triphosphate groups), the building blocks from which the DNA polymerase synthesizes a new DNA strand; a buffer solution providing a suitable chemical environment for optimum activity and stability of the DNA polymerase; bivalent cations, typically magnesium (Mg) or manganese (Mn) ions; Mg2+ is the most common, but Mn2+can be used for PCR-mediated DNA mutagenesis, as a higher Mn2+ concentration increases the error rate during DNA synthesis; monovalent cations, typically potassium (K) ions.

Embodiments of the disclosure relate to the treatment of DNA molecules with bisulfite. Treatment of DNA with bisulfite converts cytosine residues to uracil. Methods involve the protection of cytosine residues from bisulfite. Such methods are further described herein. Bisulfite treatment may be any treatment that provides $HSO_3^-$ ions, such as the treatment with salts containing $HSO_3^-$ ions, such as sodium bisulfite. In some embodiments, the DNA treated by bisulfate is single-stranded.

In some embodiments, the DNA molecules are in vitro transcribed. In vitro transcription comprises a DNA template containing a RNA polymerase promoter, such as a double-stranded RNA promoter, and ribonucleotide triphosphates (NTPs). In some embodiments, the DNA template is purified. In some embodiments, the DNA template is linear. In vitro transcription may also comprise incubating the DNA template, the RNA polymerase, and the NTPs under conditions suitable for in vitro transcription. In some embodiments, in vitro transcription comprises incubating the reaction with a buffer. In some embodiments, the buffer comprises a redox reagent and cations. In some embodiments, the redox reagent comprises dithiothreitol (DTT). In some embodiments, the cations comprise bivalent cations. In some embodiments the cations comprise magnesium cations. In some embodiments, the DNA molecule that is subjected to in vitro transcription is linear and contains a RNA polymerase promoter in the correct orientation in relation to the target sequence to be transcribed. A minimal T7 promoter, for example, comprises: TAATACGACTCAC-TATA (SEQ ID NO:1), which can be inserted at the 5' end of the target DNA. The run-off transcript will have the sequence of the 3' region following the promoter. In some embodiments, in vitro transcription comprises contacting the DNA molecule with a reaction mixture comprising RNA polymerase and NTPs under conditions suitable for in vitro transcription of the DNA molecule to produce a corresponding RNA molecule. In some embodiments, the conditions include incubating the reaction mixture at a temperature in which the polymerase is active. For example, a T7 polymerase may require a temperature that is 30-45° C. or 35-40° C. for at least 1, 2, 4, 12, or 24 hours (or any range derivable therein), or longer. In vitro transcription systems are commercially available. For example, New England Biolabs sells HiScribe™, which is an in vitro transcription kit that may be used in the methods of the disclosure. It is contemplated that any RNA polymerase may be used in this system with its corresponding promoter. In some embodiments, the RNA promoter comprises a SP6 promoter, and the RNA polymerase comprises a SP6 polymerase. In some embodiments, the RNA promoter comprises a T3 promoter and the polymerase comprises a T3 polymerase. In some embodiments, the RNA promoter comprises a T7 promoter and the polymerase comprises T7 polymerase.

Methods of the disclosure relate to embodiments utilizing adaptors that may be ligated to DNA. In some embodiments, the adaptor comprises one or more primer binding sites that can be used for sequencing, for PCR, or for real-time quantitative PCR. The adaptors may comprise one or more cloning sites that allow for additional molecular biology techniques. The adaptors may comprise a reporter gene, such as an antibiotic resistance gene or a marker gene such as a gene that provides fluorescence (green fluorescent protein and derivative thereof).

II. NUCLEIC ACID MODIFICATIONS

In certain embodiments, methods involve protection of particular cytosines or cytosine variants from bisulfite treatment, especially bisulfite-mediated deamination. The protection may include chemical modification of these variants so the readout in bisulfite sequencing of the modified sequence may be different from the unmodified control nucleic acid.

Treatment of nucleic acids with bisulfite may convert cytosine residues to uracil, but leaves 5-methylcytosine or 5-hydroxymethylcytosine residues unaffected. Thus, bisulfite treatment may introduce specific changes in the DNA sequence that depend on the methylation status of individual cytosine residues, yielding single-nucleotide resolution information about the methylation status of a segment of DNA. Various analyses can be performed on the altered sequence to retrieve this information. One objective of this analysis may be reduced to differentiating between single nucleotide polymorphisms (cytosines and thymidine or uracil) resulting from bisulfite conversion.

Certain embodiments relate to the modification of 5fC and/or 5caC to protect the cytosines from bisulfite deamination. Other embodiments relate to the modification of 5mC and/or 5hmC to render them susceptible to bisulfite deamination. Described below are exemplary modifications that can be used in the disclosed methods for various purposes, for example, for protecting the cytosines from bisulfate deamination or for the differential detection of the various cytosine modifications.

A. Modification of 5fC

Certain embodiments are directed to methods and compositions for modifying nucleic acids containing 5fC or modifying, detecting, and/or evaluating 5fC in nucleic acids. In certain aspects a nucleic acid is modified to protect 5fC from a bisulfite-mediated deamination. For example, the nucleic acid may be modified to an oxime by a compound comprising a hydroxylamine group (such as R—NH—OH), a hydrazine group (such as R—NH—NH$_2$) or a hydrazide group (such as R—C(=O)—NH—NH$_2$).

A functional group (e.g., a hydroxyamine group) may be incorporated into or attached to a nuclei acid using methods described herein. This incorporation or attachment of a functional group allows further labeling or tagging cytosine residues with biotin or tags. The labeling or tagging of 5fC can use, for example, click chemistry or other functional/coupling groups know to those skilled in the art. The labeled or tagged nucleic acid fragments containing 5fC can be enriched, isolated, detected and/or evaluated.

Hydroxylamine groups that may be used in certain aspects include those having the general formula or having a functional group having the general formula of:

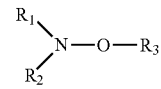

in which R$_1$, R$_2$ are hydrogen, and R$_3$ is selected from the group consisting of hydrogen, lower alkyl, and aryl; and water soluble salts of these hydroxylamines. The lower alkyl group may generally have from 1 to 8 carbon atoms and the aryl group may be, for example, phenyl, benzyl, and tolyl.

Non-limiting examples of suitable hydroxylamine-containing compounds include hydroxylamine; hydroxylamine hydrochloride; hydroxylammonium acid sulfate; hydroxylamine phosphate; O-methylhydroxylamine; O-hexylhydroxylamine; O-pentylhydroxylamine; O-benzylhydroxylamine; and particularly, O-ethylhydroxylamine (EtONH$_2$), or any O-alkylated or O-arylated hydroxylamine may be used.

Also suitable for use in certain aspects are compounds, which upon being added to the aqueous system, yield hydroxylamines.

The compound containing a hydroxylamine group may also include substituted derivatives of hydroxylamine. If the hydroxyl hydrogen is substituted, this is called an O-hydroxylamine. Similarly to ordinary amines, one can distinguish primary, secondary and tertiary hydroxylamines, the latter two referring to compounds where two or three hydrogens are substituted, respectively.

A "hydrazine group" may refer to the divalent group—NR$^1$R$^2$—NH$_2$, wherein R$^1$ and R$^2$ may be alkyl, aryl, or benzyl. As used herein, "hydrazine groups" or "hydrazine groups" include, but are not limited to, hydrazines, hydrazides, semicarbazides, carbazides, thiosemicarbazides, thiocarbazides, hydrazine carboxylates and carbonic acid hydrazines. Examples of hydrazines used herein include N-alkylhydrazine, N-arylhydrazine, N-benzylhydrazine, N,N-dialkylhydrazine, N,N-diarylhydrazine, N,N-dibenzylhydrazine, N,N-alkylbenzylhydrazine, N,N-arylbenzylhydrazine, and N,N-alkylarylhydrazine.

A "hydrazide group" may refer to a common functional group characterized by a nitrogen to nitrogen covalent bond with four substituents with at least one of them being an acyl group. The general structure for a hydrazide group may be R—C(=O)—NR 3—NH$_2$ or R—(SO$_2$)R$^3$ —NH$_2$, wherein R may be alkyl or aryl, and R 3 may be hydrogen, alkyl, aryl, or benzyl. Important members of this class are sulfonylhydrazides such as p-toluenesulfonylhydrazide which are useful reagents in organic chemistry such as in the Shapiro reaction. This reagent can be prepared by reaction of tosyl chloride with hydrazine. Examples of hydrazides used herein include-toluenesulfonylhydrazide, N-acylhydrazide, N,N-alkylacylhydrazide, N,N-b enzyl acylhy drazi de, N,N-arylacylhydrazide, N-sulfonylhydrazide, N,N-alkyl sulfonylhydrazide, N,N-b enzyl sulfonylhydrazide, and N,N-aryl sulfonylhydrazide.

B. Modification of 5caC

Certain embodiments are directed to methods and compositions for modifying nucleic acids containing 5caC. In certain aspects a target nucleic acid may be modified to protect 5caC from a bisulfate-mediated deamination. For example, the nucleic acid may be transformed into an amide by reaction with an amine-containing compound or a compound comprising an amine group.

The amine-containing compound may have a general formula of NH$_2$—R, wherein R=alkyl such as —CH$_2$CH$_3$ or —CH—(CH$_3$)$_2$; cycloalkyl, aryl, or benzyl. For example, the amine group may be alkylamine, cycloalkylamine, benzylamine, xyleneamine, or hydroxylamine. The amine-containing compound may be alkylamine, cycloalkylamine, or benzylamine. The amine group may be attached to a detected label or compound, such as a biotin.

Amine groups are functional groups that contain a basic nitrogen atom with a lone pair. Amines are derivatives of ammonia, wherein one or more hydrogen atoms have been replaced by a substituent such as an alkyl or aryl group. The compound comprising an amine group may be an aliphatic amine or an aromatic amine, a primary amine, a secondary amine, a tertiary amine, or a cyclic amine.

An aliphatic amine has no aromatic ring attached directly to the nitrogen atom. Aromatic amines have the nitrogen atom connected to an aromatic ring as in the various anilines. The aromatic ring decreases the alkalinity of the amine, depending on its substituents. The presence of an amine group strongly increases the reactivity of the aromatic ring, due to an electron-donating effect.

Amines may also be organized into four subcategories:

Primary amines—Primary amines arise when one of three hydrogen atoms in ammonia is replaced by an alkyl or aromatic. Important primary alkyl amines include methylamine, ethanolamine (2-aminoethanol), and the buffering agent tris, while primary aromatic amines include aniline.

Secondary amines—Secondary amines have two substituents (alkyl, aryl or both) bound to N together with one hydrogen. Important representatives include dimethylamine and methylethanolamine, while an example of an aromatic amine would be diphenylamine.

Tertiary amines—In tertiary amines, all three hydrogen atoms are replaced by organic substituents. Examples include trimethylamine, which has a distinctively fishy smell or triphenylamine.

Cyclic amines—Cyclic amines are either secondary or tertiary amines. Examples of cyclic amines include the 3-member ring aziridine and the six-membered ring piperidine. N-methylpiperidine and N-phenylpiperidine are examples of cyclic tertiary amines.

In certain embodiments, 5caC may be modified or labelled with an amine or thiol group using a coupling agent such as a carbodiimide derivative, i.e., a compound having a functional group consisting of the formula R$_1$N=C=NR$_2$. In particular embodiments, R$_1$ and R$_2$ are the same or different and can be alkyl or aryl. For example, the carbodiimide derivative may be 1-ethyl-3-(3-dimethylaminopropyl)carbodiimide (EDC) or N,N'-dicyclohexylcarbodiimide (DCC).

C. Modification of 5mC and/or 5hmC

In certain embodiments, 5mC and/or 5hmC in a nucleic acid may be subjected to modification, such as oxidation to 5caC. In further embodiments, oxidation of 5mC and/or to 5caC can be accomplished by contacting a nucleic acid with a methylcytosine dioxygenase (e.g., TET 1, TET2 and TET3) or an enzyme having similar activity or the catalytic domain of a methylcytosine dioxygenase; or chemical modification. The nucleic acid may be an isolated nucleic acid, a nucleic acid in a sample, a nucleic acid that has been modified by methods described above (e.g., modification of 5fC and/or 5caC), or a nucleic acid that has not been modified.

5-methylcytosine (5mC) in DNA has an important function in gene expression, genomic imprinting, and suppression of transposable elements. It is known that 5mC can be converted to 5—hydroxymethylcytosine (5hmC) by the Tet (ten eleven translocation) proteins. Accordingly, embodiments of the disclosure include methods in which 5mC is oxidized to and/or 5hmC is oxidized to 5fC and/or 5fC is oxidized to 5caC. The Tet proteins can also convert 5mC to 5-formylcytosine (5fC) and 5-carboxylcytosine (5caC) in an enzymatic activity—dependent manner (Ito et al., 2011, incorporated by reference).

Modification of 5mC can be performed using the enzymes or chemical agents, that catalyzes or cause the transfer of a modification moiety to the 5mC, yielding a modified 5mC (m5mC). This strategy is useful for incorporating modifications to 5mC for labeling or tagging in eukaryotic nucleic acids.

Chemical tagging can be used to determine the precise locations of 5mC in a high throughput manner. The inventors have shown that the 5mC modification renders the labeled DNA resistant to certain restriction enzyme digestion and/or polymerization. In certain aspects, modified and unmodified genomic DNA may be treated with restriction enzymes and subsequently subjected to various sequencing methods to reveal the precise locations of each cytosine modification that hampers the digestion.

The inventors have shown that a modification moiety, such as a functional group like an azide group, can be incorporated into DNA using methods described herein. This incorporation of a functional group allows further labeling or tagging cytosine residues with biotin and other tags. The labeling or tagging of 5mC can use, for example, click chemistry or other functional/coupling groups known to those skilled in the art. The labeled or tagged DNA fragments containing m5mC can be isolated and/or evaluated using modified methods being currently used to evaluate 5mC containing nucleic acids.

Furthermore, methods and compositions of the disclosure may be used to introduce a sterically bulky group to 5mC. The presence of a bulky group on the DNA template strand will interfere with the synthesis of a nucleic acid strand by DNA polymerase or RNA polymerase, or the efficient cleavage of DNA by a restriction endonuclease or inhibition of other enzymatic modifications of nucleic acid containing 5mC. As a result, primer extensions or other assays can be employed, for example, to evaluate a partially extended primer of certain length and the modification sites can be revealed by sequencing the partially extended primers. Other approaches taking advantage of this chemical tagging method are also contemplated.

Certain embodiments are directed to methods and compositions for modifying 5hmC, detecting 5hmC, and/or evaluating 5hmC in nucleic acids. In certain aspects, 5hmC is glycosylated. In a further aspect 5hmC is coupled to a labeled or modified glucose moiety. In certain aspects a target nucleic acid is contacted with a β-glucosyltransferase enzyme and a UDP substrate comprising a modified or modifiable glucose moiety. Using the methods described herein a large variety of detectable groups (biotin, fluorescent tag, radioactive groups, etc.) can be coupled to 5hmC via a glucose modification. Methods and compositions are described in PCT application PCT/US2011/031370, filed Apr. 6, 2011, which is hereby incorporated by reference in its entirety.

Modification of 5hmC can be performed using the enzyme β-glucosyltransferase ((βGT), or a similar enzyme, that catalyzes the transfer of a glucose moiety from uridine diphosphoglucose (UDP-Glc) to the hydroxyl group of 5hmC, yielding β-glycosyl-5-hydroxymethyl-cytosine (ghmC). The inventors have found that this enzymatic glycosylation offers a strategy for incorporating modified glucose molecules for labeling or tagging 5hmC in eukaryotic nucleic acids. For instance, a glucose molecule chemically modified to contain an azide (N3) group may be covalently attached to 5hmC through this enzyme-catalyzed glycosylation. Thereafter, phosphine-activated reagents, including but not limited to biotin-phosphine, fluorophore-phosphine, and NHS-phosphine, or other affinity tags can be specifically installed onto glycosylated 5hmC via reactions with the azide.

5mC and/or 5hmC can be directly or indirectly modified with a number of functional groups or labeled molecules. One example is the oxidation of 5mC and the subsequent labeling with a functionalized or labeled glucose molecule. In certain embodiments, 5mC can be first modified with a modification moiety or a functional group prior to being further modified by the attachment of a glucosyl moiety.

In additional embodiments, a functionalized or labeled glucose molecule can be used in conjunction with βGT to modify 5hmC in a nucleic polymer such as DNA or RNA. In certain aspects, the βGT UDP substrate comprises a functionalized or labeled glucose moiety.

In a further aspect, the modification moiety can be modified or functionalized using click chemistry or other coupling chemistries known in the art. Click chemistry is a chemical philosophy introduced by K. Barry Sharpless in 2001 (Kolb et al., 2001; Evans, 2007) and describes chemistry tailored to generate substances quickly and reliably by joining small units.

The inventors have shown that a functional group (e.g., an azide group) can be incorporated into DNA using methods described herein. This incorporation of a functional group allows further labeling or tagging cytosine residues with biotin and other tags. The labeling or tagging of 5hmC can use, for example, click chemistry or other functional/coupling groups know to those skilled in the art. The labeled or tagged DNA fragments containing 5hmC can be isolated and/or evaluated using modified methods being currently used to evaluate 5mC containing nucleic acids.

In certain aspects, differential modification of nucleic acid between two or more samples can be evaluated. Studies including heart, liver, lungs, kidney, muscle, testes, spleen, and brain indicate that under normal conditions 5hmC is predominately in normal brain cells. Evaluating and comparing 5hmC levels can be used in evaluating various disease states and comparing various nucleic acid samples.

D. TET proteins

The ten-eleven translocation (TET) proteins are a family of DNA hydroxylases that have been discovered to have enzymatic activity toward the methyl group on the 5-position of cytosine (5-methylcytosine [5mC]). The TET protein family includes three members, TET1, TET2, and TET3. TET proteins are believed to have the capacity of converting 5mC into 5-hydroxymethylcytosine (5hmC), 5-formylcytosine (5fC), and 5-carboxylcytosine (5caC) through three consecutive oxidation reactions.

The first member of TET family proteins, TET1 gene, was first detected in acute myeloid leukemia (AML) as a fusion partner of the histone H3 Lys 4 (H3K4) methyltransferase MLL (mixed-lineage leukemia) (Ono et al., 2002; Lorsbach et al., 2003). It has been first discovered that human TET1 protein possesses enzymatic activity capable of hydroxylating to generate 5hmC (Tahiliani et al., 2009). Later on, all members of the mouse TET protein family (TET 1-3) have been demonstrated to have 5mC hydroxylase activities (Ito et al., 2010).

TET proteins generally possess several conserved domains, including a CXXC zinc finger domain which has high affinity for clustered unmethylated CpG dinucleotides, a catalytic domain that is typical of Fe(II)- and 2-oxoglutarate (2OG)-dependent dioxygenases, and a cysteine-rich region (Wu and Zhang, 2011, Tahiliani et al., 2009).

In some embodiments, it is contemplated that TET1, TET2, or TET3 are human or mouse proteins. Human TET1 has accession number NM 030625.2; human TET2 has accession number NM 001127208.2, alternatively, NM 017628.4; and human TET3 has accession number NM 144993.1. Mouse TET1 has accession number NM 027384.1; mouse TET2 has accession number NM 001040400.2; and mouse TET3 has accession number NM_183138.2.

E. β-glycosyltransferase (β-GT)

A glucosyl-DNA beta-glucosyltransferase (EC 2.4.1.28, β-glycosyltransferase ((βGT)) is an enzyme that catalyzes the chemical reaction in which a beta-D-glucosyl residue is transferred from UDP-glucose to a glucosylhydroxymethylcytosine residue in a nucleic acid. This enzyme resembles DNA beta-glucosyltransferase in that respect. This enzyme belongs to the family of glycosyltransferases, specifically the hexosyltransferases. The systematic name of this enzyme class is UDP-glucose:D-glucosyl-DNA beta-D-glucosyltransferase. Other names in common use include T6-glucosyl-HMC-beta-glucosyl transferase, T6-beta-glucosyl transferase, uridine diphosphoglucose-glucosyldeoxyribonucleate, and beta-glucosyltransferase.

In certain aspects, the a β-glucosyltransferase is a His-tag fusion protein having the amino acid sequence (β-GT begins at amino acid 25(met)): SHHHHEIHSSGVDLGTEN-LYFQSNAMKIAIINMGNNVINFKTVPS-SETIYLFKVISEMG LNVDIISLKNGVYTKSFDEVDVN-DYDRLIVVNS SINFFGGKPNLAILSAQKFMAKYKS KIYYLFTDIRLPF SQ SWPNVKNRPWAYLYTEEEL-LIKSPIKVISQGINLDIAKAAHKKV DNVIEFEYFPIEQYKIHMNDFQL SKPTKKTLD-VIYGGSFRSGQRESKMVEFLFDTGLNI EFFGNAREKQFKNPKYPWTKAPVF TGKIPMNMVSEKNSQAIAALIIGDKNYNDNFIT LRVWETMASDAVMLIDEEFDTKHRIINDARF YVNN-RAELIDRVNELKHSDVLRKEM LSIQHDILNKTRAK-KAEWQDAFKKAIDL (SEQ ID NO:2).

F. Functional Groups

Nucleic acids, especially cytosines and/or modified cytosines can be directly or indirectly modified (or further modified) with a number of functional groups or labeled molecules. One example is the oxidation of 5mC and the subsequent labeling with a functionalized, protectant, or labeled glucose molecule. In certain embodiments, 5mC can be first modified with a modification moiety or a functional group prior to being further modified by the attachment of a glucosyl moiety.

In additional embodiments, a functionalized or labeled glucose molecule can be used in conjunction with βGT to modify 5hmC in a nucleic polymer such as DNA or RNA. In certain aspects, the βGT UDP substrate comprises a functionalized or labeled glucose moiety.

In a further aspect, the modification moiety can be modified or functionalized using click chemistry or other coupling chemistries known in the art. Click chemistry is a chemical philosophy introduced by K. Barry Sharpless in 2001 (Kolb et al., 2001; Evans, 2007) and describes chemistry tailored to generate substances quickly and reliably by joining small units.

Chemical reactions that lead to a covalent linkage include, for example, cycloaddition reactions (such as the Diels-Alder's reaction, the 1,3-dipolar cycloaddition Huisgen reaction, and the similar "click reaction"), condensations, nucleophilic and electrophilic addition reactions, nucleophilic and electrophilic substitutions, addition and elimination reactions, alkylation reactions, rearrangement reactions and any other known organic reactions that involve a functional group.

Representative examples of functional groups include, without limitation, acyl halide, aldehyde, alkoxy, alkyne, amide, amine, aryloxy, azide, aziridine, azo, carbamate, carbonyl, carboxyl, carboxylate, cyano, diene, dienophile, epoxy, guanidine, guanyl, halide, hydrazide, hydrazine, hydroxy, hydroxylamine, imino, isocyanate, nitro, phosphate, phosphonate, sulfinyl, sulfonamide, sulfonate, thioalkoxy, thioaryloxy, thiocarbamate, thiocarbonyl, thiohydroxy, thiourea and urea, as these terms are defined hereinafter.

Exemplary first and second functional groups that are chemically compatible with one another as described herein include, but are not limited to, hydroxy and carboxylic acid, which form an ester bond; thiol and carboxylic acid, which form a thioester bond; amine and carboxylic acid, which form an amide bond; aldehyde and amine, hydrazine, hydrazide, hydroxylamine, phenylhydrazine, semicarbazide or thiosemicarbazide, which form a Schiff base (imine bond); alkene and diene, which react therebetween via cycloaddition reactions; and functional groups that can participate in a Click reaction.

Further examples of pairs of functional groups capable of reacting with one another include an azide and an alkyne, an unsaturated carbon-carbon bond (e.g., acrylate, methacrylate, maleimide) and a thiol, an unsaturated carbon-carbon bond and an amine, a carboxylic acid and an amine, a hydroxyl and an isocyanate, a carboxylic acid and an isocyanate, an amine and an isocyanate, a thiol and an isocyanate. Additional examples include an amine, a hydroxyl, a thiol or a carboxylic acid along with a nucleophilic leaving group (e.g., hydroxysuccinimide, a halogen).

In some embodiments, the functional groups can be latent groups, which are exposed during the chemical reaction, such that the reacting (e.g., covalent bond formation) is effected once a latent group is exposed. Exemplary such groups include, but are not limited to, functional groups as described hereinabove, which are protected with a protecting group that is labile under selected reaction conditions.

Examples of labile protecting groups include, for example, carboxylate esters, which may hydrolyzed to form an alcohol and a carboxylic acid by exposure to acidic or basic conditions; silyl ethers such as trialkyl silyl ethers, which can be hydrolysed to an alcohol by acid or fluoride ion; p-methoxybenzyl ethers, which may be hydrolysed to an alcohol, for example, by oxidizing conditions or acidic conditions; t-butyloxycarbonyl and 9-fluorenylmethyloxycarbonyl, which may be hydrolysed to an amine by a exposure to basic conditions; sulfonamides, which may be hydrolysed to a sulfonate and amine by exposure to a suitable reagent such as samarium iodide or tributyltin hydride; acetals and ketals, which may be hydrolysed to form an aldehyde or ketone, respectively, along with an alcohol or diol, by exposure o acidic conditions; acylals (i.e., wherein a carbon atom is attached to two carboxylate groups), which may be hydrolysed to an aldehyde of ketone, for example, by exposure to a Lewis acid; orthoesters (i.e., wherein a carbon atom is attached to three alkoxy or aryloxy groups), which may be hydrolysed to a carboxylate ester (which may be further hydrolysed as described hereinabove) by exposure to mildly acidic conditions; 2-cyanoethyl phosphates, which may be converted to a phosphate by exposure to mildly basic conditions; methylphosphates, which may be hydrolysed to phosphates by exposure to strong nucleophiles; phosphates, which may be hydrolysed to alcohols, for example, by exposure to phosphatases; and aldehydes, which may be converted to carboxylic acids, for example, by exposure to an oxidizing agent.

According to some embodiments of the current disclosure, a linking moiety is formed as a result of a bond-forming reaction between two (first and second) functional groups.

Exemplary linking moieties, according to some embodiments of the present invention, which are formed between a first and a second functional groups as described herein include without limitation, amide, lactone, lactam, carboxylate (ester), cycloalkene (e.g., cyclohexene), heteroalicyclic, heteroaryl, triazine, triazole, disulfide, imine, aldimine, ketimine, hydrazone, semicarbazone and the likes. Other linking moieties are defined hereinbelow.

For example, a reaction between a diene functional group and a dienophile functional group, e.g. a Diels-Alder reaction, would form a cycloalkene linking moiety, and in most cases a cyclohexene linking moiety. In another example, an amine functional group would form an amide linking moiety when reacted with a carboxyl functional group. In another example, a hydroxyl functional group would form an ester linking moiety when reacted with a carboxyl functional group. In another example, a sulfhydryl functional group would form a disulfide (—S—S—) linking moiety when reacted with another sulfhydryl functional group under oxidation conditions, or a thioether (thioalkoxy) linking moiety when reacted with a halo functional group or another leaving-functional group. In another example, an alkynyl functional group would form a triazole linking moiety by "click reaction" when reacted with an azide functional group.

The "click reaction", also known as "click chemistry" is a name often used to describe a stepwise variant of the Huisgen 1,3-dipolar cycloaddition of azides and alkynes to yield 1,2,3-triazole. This reaction is carried out under ambient conditions, or under mild microwave irradiation, typically in the presence of a Cu(I) catalyst, and with exclusive regioselectivity for the 1,4-disubstituted triazole product when mediated by catalytic amounts of Cu(I) salts [V. Rostovtsev, L. G. Green, V. V. Fokin, K. B. Sharpless, Angew. Chem. Int. Ed. 2002, 41, 2596; H. C. Kolb, M. Finn, K. B. Sharpless, Angew Chem., Int. Ed. 2001, 40, 2004].

The "click reaction" is particularly suitable in the context of embodiments of the present invention since it can be carried out under conditions which are non-destructive to DNA molecules, and it affords attachment of a labeling agent to 5hmC in a DNA molecule at high chemical yields using mild conditions in aqueous media. The selectivity of this reaction allows to perform the reaction with minimized or nullified use of protecting groups, which use often results in multistep cumbersome synthetic processes.

G. Transposone labeling of DNA

In certain aspects the nucleic acid molecule is tagged with a transposon. For example, the nucleic acid molecule may be contacted with a transposon and a transposase to allow for the non-specific integration of the transposon into the nucleic acid molecule.

As used throughout, the term transposon refers to a double-stranded DNA that contains the nucleotide sequences that are necessary to form the complex with the transposase or integrase enzyme that is functional in an in vitro transposition reaction. A transposon forms a complex or a synaptic complex or a transposome complex. The transposon can also form a transposome composition with a transposase or integrase that recognizes and binds to the transposon sequence, and which complex is capable of inserting or transposing the transposon into target DNA with which it is incubated in an in vitro transposition reaction.

Tagging the nucleic acid molecule with a transposon may also include fragmenting the tagged DNA. In some embodiments, a transposase may be used to catalyze integration of oligonucleotides into a target nucleic acid at high density (e.g. at about every 300 base pairs). For example, a transposase, such as Nextera's TRANSPOSOME™ technology, may be used to generate random dsDNA breaks. The TRANSPOSOME™ complex includes free transposon ends and a transposase. When this complex is incubated with dsDNA, the DNA is fragmented and the transferred strand of the transposon end oligonucleotide is covalently attached to the end of the DNA fragment. In some embodiments, it is attached to the 3' end. In some embodiments, it is attached to the 5' end. In some applications, the transposon ends may be appended with primer sites. By varying buffer and reaction conditions (e.g., concentration of TRANSPOSOME™ complexes), the size distribution of the fragmented and tagged DNA library may be controlled.

In some embodiments, the transposon further comprises a label or affinity tag, such as biotin. Other affinity tags include E-tag, Flag-tag, HA-tag, His-tag, Myc-tag, etc. In some embodiments, the affinity tag is attached to the end of the P7 adapter. In some embodiments, the affinity tag is attached to the 5' end of the adapter.

III. SEQUENCING METHODS

A. Massively parallel signature sequencing (MPSS).

The first of the next-generation sequencing technologies, massively parallel signature sequencing (or MPSS), was developed in the 1990s at Lynx Therapeutics. MPSS was a bead-based method that used a complex approach of adapter ligation followed by adapter decoding, reading the sequence in increments of four nucleotides. This method made it susceptible to sequence-specific bias or loss of specific sequences. Because the technology was so complex, MPSS was only performed 'in-house' by Lynx Therapeutics and no DNA sequencing machines were sold to independent laboratories. Lynx Therapeutics merged with Solexa (later acquired by Illumina) in 2004, leading to the development of sequencing-by-synthesis, a simpler approach acquired from Manteia Predictive Medicine, which rendered MPSS obsolete. However, the essential properties of the MPSS output were typical of later "next-generation" data types, including hundreds of thousands of short DNA sequences. In the case of MPSS, these were typically used for sequencing cDNA for measurements of gene expression levels. Indeed, the powerful Illumina HiSeq2000, HiSeq2500 and MiSeq systems are based on MPSS.

B. Polony sequencing.

The Polony sequencing method, developed in the laboratory of George M. Church at Harvard, was among the first next-generation sequencing systems and was used to sequence a full genome in 2005. It combined an in vitro paired-tag library with emulsion PCR, an automated microscope, and ligation-based sequencing chemistry to sequence an E. coli genome at an accuracy of >99.9999% and a cost approximately 1/9 that of Sanger sequencing. The technology was licensed to Agencourt Biosciences, subsequently spun out into Agencourt Personal Genomics, and eventually incorporated into the Applied Biosystems SOLiD platform, which is now owned by Life Technologies.

C. 454 pyrosequencing.

A parallelized version of pyrosequencing was developed by 454 Life Sciences, which has since been acquired by Roche Diagnostics. The method amplifies DNA inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA, and the combined data are used to generate sequence readouts. This technology provides intermediate read length and price per base compared to Sanger sequencing on one end and Solexa and SOLiD on the other.

D. Illumina (Solexa) sequencing.

Solexa, now part of Illumina, developed a sequencing method based on reversible dye-terminators technology, and engineered polymerases, that it developed internally. The terminated chemistry was developed internally at Solexa and the concept of the Solexa system was invented by Balasubramanian and Klennerman from Cambridge University's chemistry department. In 2004, Solexa acquired the company Manteia Predictive Medicine in order to gain a massively parallel sequencing technology based on "DNA Clusters", which involves the clonal amplification of DNA on a surface. The cluster technology was co-acquired with Lynx Therapeutics of California. Solexa Ltd. later merged with Lynx to form Solexa Inc.

In this method, DNA molecules and primers are first attached on a slide and amplified with polymerase so that local clonal DNA colonies, later coined "DNA clusters", are formed. To determine the sequence, four types of reversible terminator bases (RT-bases) are added and non-incorporated nucleotides are washed away. A camera takes images of the fluorescently labeled nucleotides, then the dye, along with the terminal 3' blocker, is chemically removed from the DNA, allowing for the next cycle to begin. Unlike pyrosequencing, the DNA chains are extended one nucleotide at a time and image acquisition can be performed at a delayed moment, allowing for very large arrays of DNA colonies to be captured by sequential images taken from a single camera.

Decoupling the enzymatic reaction and the image capture allows for optimal throughput and theoretically unlimited sequencing capacity. With an optimal configuration, the ultimately reachable instrument throughput is thus dictated solely by the analog-to-digital conversion rate of the camera, multiplied by the number of cameras and divided by the number of pixels per DNA colony required for visualizing them optimally (approximately 10 pixels/colony). In 2012, with cameras operating at more than 10 MHz A/D conversion rates and available optics, fluidics and enzymatics, throughput can be multiples of 1 million nucleotides/second, corresponding roughly to one human genome equivalent at 1× coverage per hour per instrument, and one human genome re-sequenced (at approx. 30×) per day per instrument (equipped with a single camera).

E. SOLiD sequencing.

Applied Biosystems' (now a Life Technologies brand) SOLiD technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting beads, each containing single copies of the same DNA molecule, are deposited on a glass slide. The result is sequences of quantities and lengths comparable to Illumina sequencing. This sequencing by ligation method has been reported to have some issue sequencing palindromic sequences.

F. Ion Torrent semiconductor sequencing.

Ion Torrent Systems Inc. (now owned by Life Technologies) developed a system based on using standard sequencing chemistry, but with a novel, semiconductor based detection system. This method of sequencing is based on the detection of hydrogen ions that are released during the polymerization of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

G. DNA nanoball sequencing.

DNA nanoball sequencing is a type of high throughput sequencing technology used to determine the entire genomic sequence of an organism. The company Complete Genomics uses this technology to sequence samples submitted by independent researchers. The method uses rolling circle replication to amplify small fragments of genomic DNA into DNA nanoballs. Unchained sequencing by ligation is then used to determine the nucleotide sequence. This method of DNA sequencing allows large numbers of DNA nanoballs to be sequenced per run and at low reagent costs compared to other next generation sequencing platforms. However, only short sequences of DNA are determined from each DNA nanoball which makes mapping the short reads to a reference genome difficult. This technology has been used for multiple genome sequencing projects and is scheduled to be used for more.

H. Heliscope single molecule sequencing.

Heliscope sequencing is a method of single-molecule sequencing developed by Helicos Biosciences. It uses DNA fragments with added poly-A tail adapters which are attached to the flow cell surface. The next steps involve extension-based sequencing with cyclic washes of the flow cell with fluorescently labeled nucleotides (one nucleotide type at a time, as with the Sanger method). The reads are performed by the Heliscope sequencer. The reads are short, up to 55 bases per run, but recent improvements allow for more accurate reads of stretches of one type of nucleotides. This sequencing method and equipment were used to sequence the genome of the M13 bacteriophage.

Single Molecule Real Time (SMRT) Sequencing.

SMRT sequencing is based on the sequencing by synthesis approach. The DNA is synthesized in zero-mode waveguides (ZMWs)—small well-like containers with the capturing tools located at the bottom of the well. The sequencing is performed with use of unmodified polymerase (attached to the ZMW bottom) and fluorescently labelled nucleotides flowing freely in the solution. The wells are constructed in a way that only the fluorescence occurring by the bottom of the well is detected. The fluorescent label is detached from the nucleotide at its incorporation into the DNA strand, leaving an unmodified DNA strand. According to Pacific Biosciences, the SMRT technology developer, this methodology allows detection of nucleotide modifications (such as cytosine methylation). This happens through the observation of polymerase kinetics. This approach allows reads of 20,000 nucleotides or more, with average read lengths of 5 kilobases.

IV. METHODS OF USE

A. Identification of DNA Methylation Variants

The field of DNA methylation analysis has expanded recently with the identification of multiple cytosine variants. Traditional DNA methylation involves the transfer of a methyl group to the carbon 5 position of cytosine to produce 5-methylcytosine (5mC). However, research has shown that the Tet family of cytosine oxygenase enzymes are involved in oxidizing 5-methylcytosine into 5-hydroxymethylcytosine (5hmC), 5-formylcytosine (5fC) and 5-carboxylcytosine (5caC).

5-Formylcytosine (5fC) is one of the DNA variants that is produced when Tet enzymes act on 5-hydroxymethylcytosine. Further oxidation of 5-formylcytosine by the Tet enzyme will results in conversion to 5-carboxylcytosine. It is believed that the oxidation of 5-methylcytosine through the various DNA methylation variants represents a mechanism of DNA demethylation, and that this demethylation pathway has a function during development and germ cell programming. 5-Formylcytosine is present in mouse embryonic stem (ES) cells and major mouse organs. This DNA modification also appears in the paternal pronucleus post-fertilization, concomitant with the disappearance of 5-methylcytosine, suggesting its involvement in the DNA demethylation process.

5-Carboxylcytosine (5caC) has been identified as one of the DNA methylation variants that is produced when Tet enzymes oxidize 5-hydroxymethylcytosine and, subsequently 5-formylcytosine. It is believed that the oxidation of 5-methylcytosine through to represents a mechanism of DNA demethylation, and that this demethylation pathway has a function during development and germ cell programming. It has been suggested that 5caC is excised from genomic DNA by thymine DNA glycosylase (TDG), which returns the cytosine residue back to its unmodified state.

5-Carboxylcytosine has been identified in mouse embryonic stem (ES) cells. This DNA modification appears in the paternal pronucleus post-fertilization, concomitant with the disappearance of 5-methylcytosine, further lending support that this variant is part of a DNA demethylation pathway.

5-Methylcytosine (5mC) is the DNA modification that results from the transfer of a methyl group from S-adenosyl methionine (also known as AdoMet or SAM) to the carbon 5 position of a cytosine residue. This transfer is catalyzed by DNA methyltransferase enzymes (DNMTs). 5-Methylcytosine is the most common and widely studied form of DNA methylation. It usually occurs within CpG dinucleotide motifs, although non-CpG methylation has been identified in embryonic stem cells.

5-Hydroxymethylcytosine (5hmC) is a DNA methylation modification that occurs as a result of enzymatic oxidation of 5-methylcytosine (5mC) by the Tet family of iron-dependent deoxygenases3. 5-Hydroxymethylcytosine can be found in elevated amounts in certain mammalian tissues, such as mouse Purkinje cells and granule neurons. Alternatively, 5hmC may be produced by the addition of formaldehyde to DNA cytosines by DNMT proteins.

Other methods for distinguishing epigenetic modifications have been provided. It is contemplated that the current methods can be applied and combined with other methods disclosed in the art. Examples of methods disclosed in the art include U.S. provisional patent application 61/656,924, U.S. patent application Ser. No. 13/095,505, U.S. provisional patent application 61/321,198, PCT application PCT/US2011/031370, PCT application No. PCT/US2012/032489, U.S. provisional patent application 61/472,435, provisional patent application 61/512,334, PCT application PCT/US2014/032997, and PCT application PCT/US2018/021591, US publication 20140178881, each of which are hereby incorporated by reference in their entirety. In some embodiments, the current methods may include or exclude steps described in the above-referenced patent applications.

B. Clinical and Diagnostic Applications

The methods of the disclosure may be useful for evaluating DNA for clinical and/or diagnostic purposes. Certain embodiments relate to a method for evaluating a sample comprising DNA molecules. The evaluation may be the detection or determination of a particular cytosine modification or the differential detection or determination of a particular modification.

The sample may be from a biopsy such as from fine needle aspiration, core needle biopsy, vacuum assisted biopsy, incisional biopsy, excisional biopsy, punch biopsy, shave biopsy or skin biopsy. In certain embodiments the sample is obtained from a biopsy from cancerous tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is colorectal. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. In some embodiments, the sample comprises cell-free DNA. In some embodiments, the sample comprises a fertilized egg, a zygote, a blastocyst, or a blastomere. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

In some embodiments, the methods of the disclosure can be used in the discovery of novel biomarkers for a disease or condition. In some embodiments, the methods of the disclosure can performed on a sample from a patient to provide a prognosis for a certain disease or condition in the patient. In some embodiments, the methods of the disclosure can be performed on a sample from a patient to predict the patient's response to a particular therapy. In some embodiments, the disease comprises a cancer. For example, the cancer may be pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye Cancer, intraocular melanoma eye Cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, melanoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

In some embodiments, the cancer comprises ovarian, prostate, colon, or lung cancer. In some embodiments, the method is for determining novel biomarkers for ovarian, prostate, colon, or lung cancer by evaluating cell-free DNA using methods of the disclosure. In some embodiments, the methods of the disclosure may be used on fetal DNA isolated from a pregnant female. In some embodiments, the methods of the disclosure may be used for prenatal diagnostics using fetal DNA isolated from a pregnant female. In some embodiments, the methods of the disclosure may be used for the evaluation of a fertilized embryo, such as a zygote or a blastocyst for the determination of embryo quality or for the presence or absence of a particular disease marker.

V. KITS

The invention additionally provides kits for performing the methods of the disclosure. The contents of a kit can include one or more reagents described throughout the disclosure and/or one or more reagents known in the art for performing one or more steps described throughout the disclosure. For example, the kits may include one or more of the following: ligase buffer, ligase, T4 ligase, ampligase, nuclease-free water, one or more primers, SPRI beads, crouding agent, polyethylene glycol, magnetic beads, DNA polymerase, taq polymerase, dNTPs, DNA polymerase buffer, bivalent cations, monovalent cations, bisulfite, sodium bisulfite, RNA polymerase, DTT, redox reagent, Mg2+, K+, adaptors, DNA adaptors, DNA comprising a RNA promoter, primers complementary and/or capable of annealing (at least partially) to a DNA template described herein, a protease, NTPs, an oxidant, a dioxygenase, a compound comprising a hydroxylamine group, a hydrazine group, or a hydrazide group, a compound comprising an amine group, a 3' end-blocked molecule, reverse transcriptase, glucose or modified glucose, and/or (3-glucosyltransferase.

The kits may include a 5mC or 5hmC modifying agent or agents, e.g., TET, βGT, modification moiety, etc.

One or more reagent is preferably supplied in a solid form or liquid buffer that is suitable for inventory storage, and later for addition into the reaction medium when the method of using the reagent is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

Each kit may also include additional components that are useful for amplifying the nucleic acid, or sequencing the nucleic acid, or other applications of the present disclosure as described herein. The kit may optionally provide additional components that are useful in the procedure. These optional components include buffers, capture reagents, developing reagents, labels, reacting surfaces, means for detection, control samples, instructions, and interpretive information.

VI. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of certain embodiments, are provided as an example, and are not intended as limitations on the scope of the invention. Changes therein and other uses which are encompassed within the spirit of the invention as defined by the scope of the claims will occur to those skilled in the art.

Example 1: Linear Amplification Bisulfite Sequencing for Circulating Cell-Free DNA Cancer Detection Cell-free DNA (cfDNA) in peripheral blood is known to derived from apoptosis and necrosis of cells.[1] In cancer patients, it carries the contribution of tumor cells and specific tissue cells apart from hematopoietic lineage cells. These tumor DNA fragments shed into bloodstream enables tracing cell-of-origin and provides the possibility to be a minimal invasive liquid biopsy marker for solid tumors.[2] In addition, cfDNA can be repeatedly sampled and monitored, and are impervious to intra-tumoral heterogeneity in tissue biopsy. These advantages, together with higher patient compliance and clinical convenience, grant cfDNA the potential to make great improvements in the screening, diagnosis and prognosis of cancer.[3,4]

Besides the detection of point mutation or copy number aberrations (CNV), 2, 5, 6 epigenetic markers like DNA methylation could serve in a complementary and valuable way. DNA methylation 5mC is a chemically stable epigenetic modification in relatively high abundance that has long been recognized to regulate gene expression. In tumorigenesis, hyper-methylation at promoters could lead to silencing of tumor suppressor genes; similarly, hypo-methylation of oncogenes could promote disease progression.[7-9] The aberrant methylation features are likely to act as the most sensitive and earliest indicators at early stage even precancerosis.

Recent researches used WGBS, RRBS, MCTA and MIP-seq in companion with algorithms like random forest, logistic regression and constructing probalistic model to explore potential methylation markers in cfDNA.[5, 10-14] However, when addressing precious ultra-low input clinical specimens, sensitivity barriers and extensive DNA degradation may cause sharply limited useful reads and poor data quality along with high sequencing cost. Whole genome amplification (WGA) can amplify tiny amount of cfDNA into large scale. MDA (Multiple Displacement Amplification), a widely-used hyperbranch strand displacement exponential amplification WGA technology,[15, 16] can provide almost complete genome coverage, but it displays unescapable bias and error accumulation in an exponential manner. In addition, the low efficiency when amplifying fragmented DNA makes it unable to work on cfDNA.[17, 18] Instead, the inventors marked T7 in vitro transcription, since the linear amplification not only have uniform coverage of whole genome, but also display less amplification bias comparing to MDA. Most importantly, it can ideally integrated with cfDNA fragments effectively to overcome the obstacles in liquid biopsy study.[19]

To reliably obtain robust and accurate base resolution information from rare clinical specimens, herein, the inventors developed T7-linear amplification based BS-seq (LABS-seq) for sub-nanogram liquid biopsy materials. LABS-seq can linearly generate multiple copies of RNA transcripts from 5'- to 3'-ends of cfDNA fragments or to the BS damaged nicking bases, provide greater preservation of methylome information, accurate presentation of 5mC status and more uniform amplification of whole genome. The method that displays better CpGs and genome coverage with less input materials was applied to colon cancer cfDNA markers identification and tissue-of-origin analysis.

A. Results

1. Design of LABS-Seq Strategy

To enable T7 amplification after bisulfite conversion, the inventors first ligated a fully methylated T7 adaptor (replacing all C with 5mC) to both ends of the DNA fragments and then subjected the ligation product to bisulfite (BS) conversion (FIG. 1A). The adaptor incorporated a promoter sequence for T7 RNA polymerase and a 3'-end blocked short helper to form partial double-stranded DNA structure that assists ligation. During bisulfite (BS) treatment, Cs were converted into U, whereas 5mCs were reserved and in this way the T7 promoter sequence was kept intact. The promoter regions were then annealed with a complementary T7 primer to initiate in vitro transcription. Due to the unbiased linear amplification of in vitro transcription, trace amounts of DNA fragments could be evenly amplified into multiple RNA copies. Finally, these sufficient amounts of RNA products were subjected to reverse transcription, followed by library construction for sequencing.

2. Evaluation of LABS-Seq Performance

The inventors evaluated LABS-seq on E14Tg2a mouse embryonic stem cells (ESCs) genomic DNA (gDNA). mESCs libraries starting with 100 ng, 10 ng, 1 ng, 100 pg gDNA respectively were sequenced by Illumina NextSeq 500 SE75 and performed the systematic comparison for LAB S-seq to other two commercial available WGBS-seq methods, MethylC-seq (pre-BS) and EpiGnome (post-BS). The inventors further performed 50 pg, 20 pg, 10 pg mESCs libraries with biological replicates in the same way to investigate technical limitation of LABS-seq.

Figure 1B:
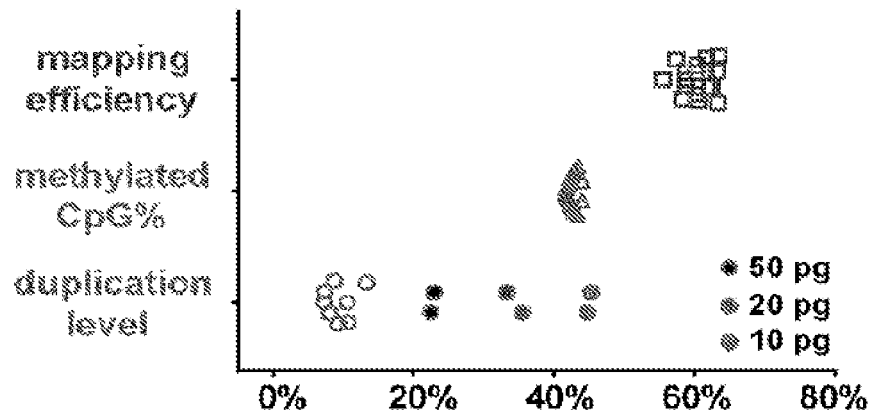
Figure 1B:
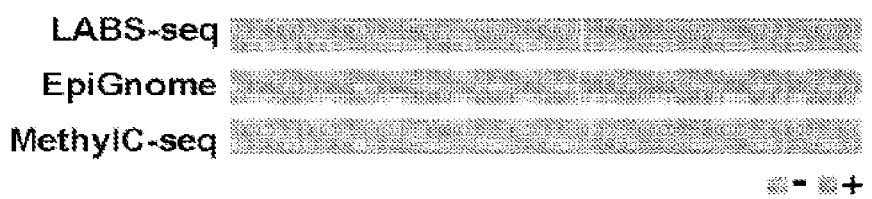
Figure 1C:
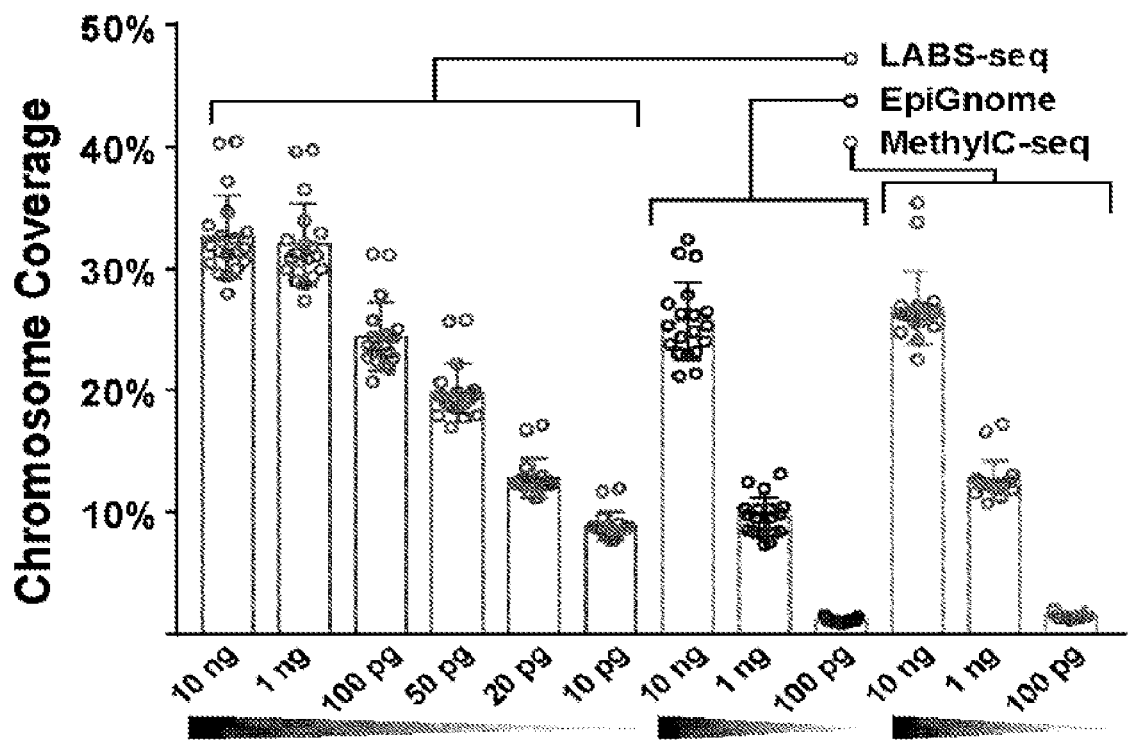
Figure 2A:
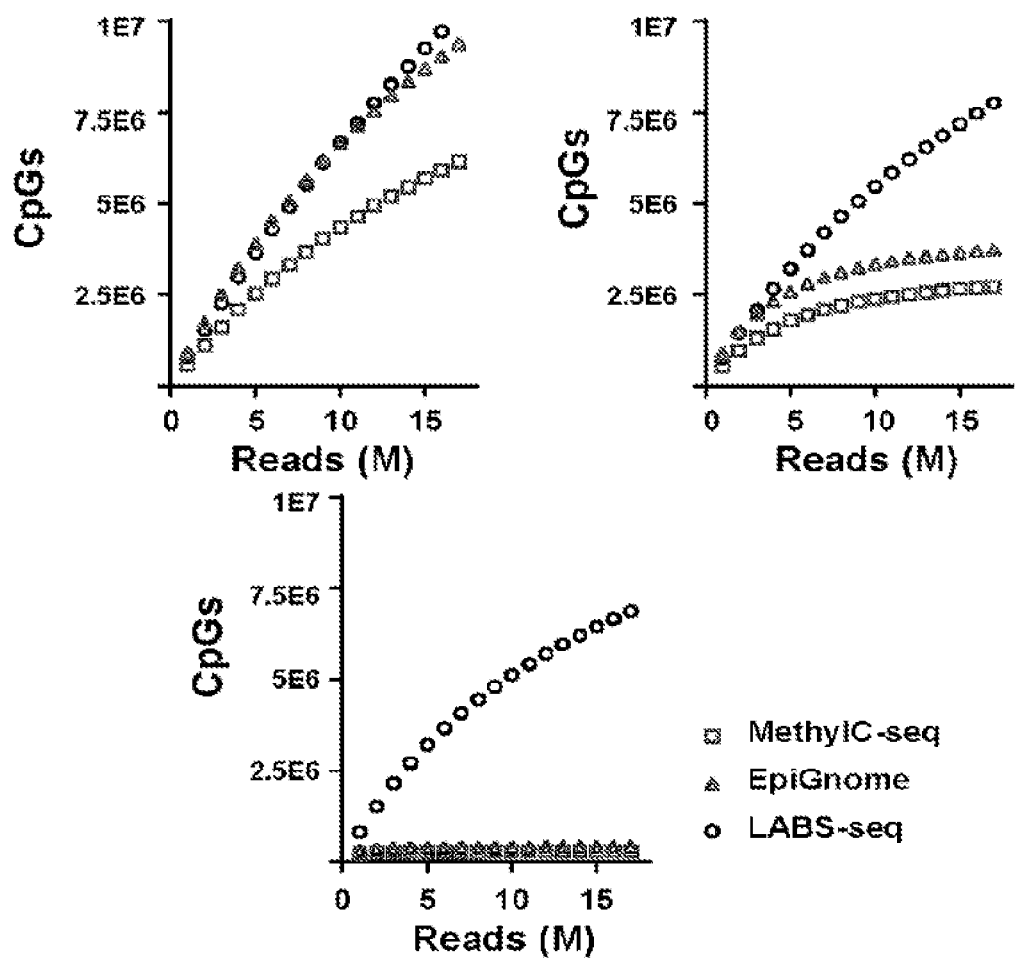
FIGS. 2A-C. (A) Saturation plot of LAB S-seq, EpiGnome and MethylC-seq illustrating the relationship between CpG coverage and sequencing depth. Plots show the number of unique CpGs covered (y axis) as a function of aligned reads (x axis). (B) GC content bias of the three methods. (C) Amplification uniformity by Lorenz curve of cumulative fraction of reads vs. cumulative fractions of genome. Perfectly uniform coverage leads to the diagonal line, and deviation from the diagonal line represents amplification bias.
Figure 7A:
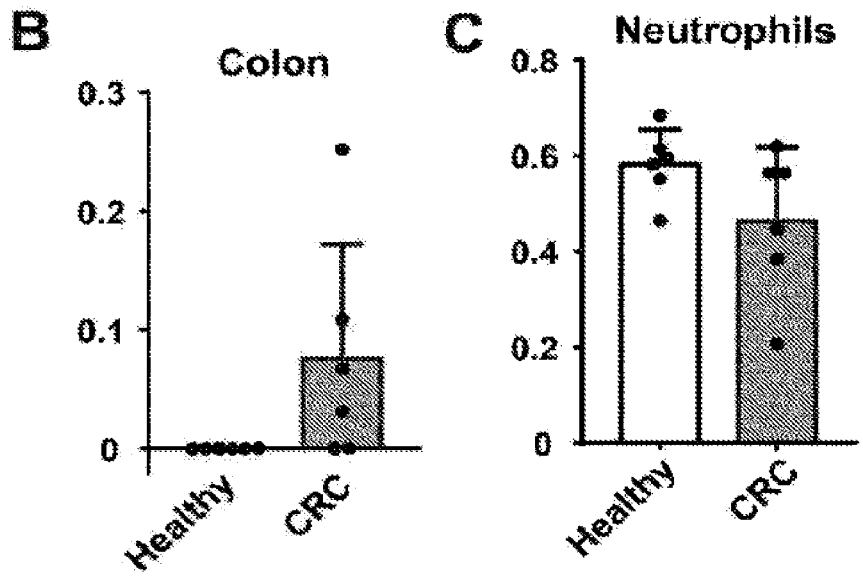
FIGS. 7A-B. (A) Genome coverage comparison among LABS-seq (Bars 1-6), MethylC-seq (Bars 10-12) and EpiGnome (Bars 7-9). (B) CpGs numbers comparison among LABS-seq (Bars 1-6), MethylC-seq (Bars 10-12) and EpiGnome.
Figure 7A:
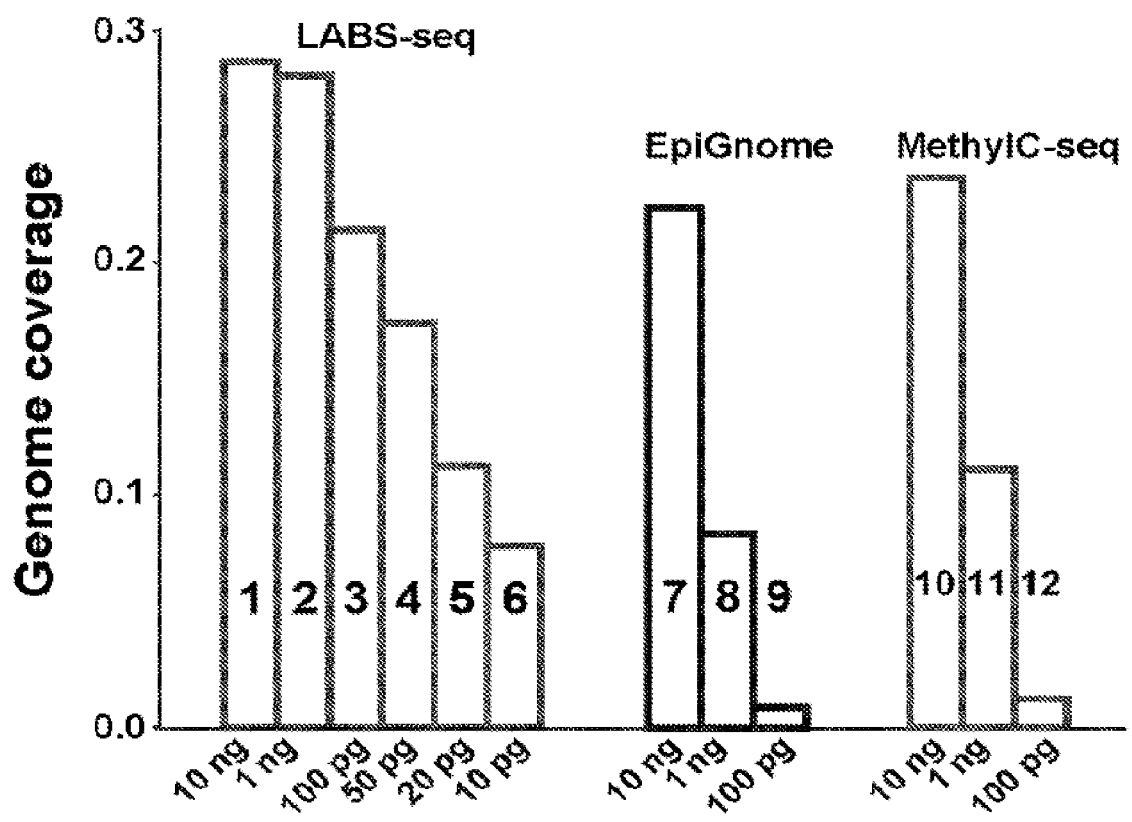
Figure 7B:
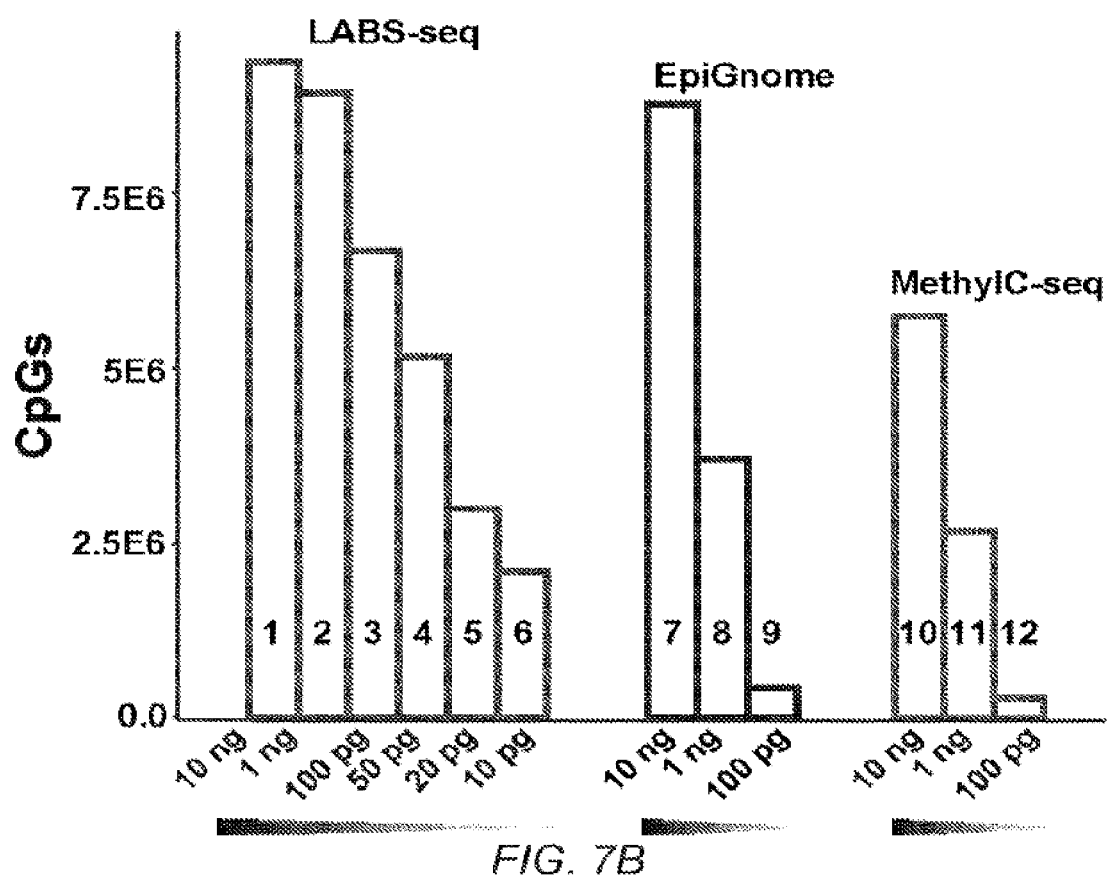
Figure 8:
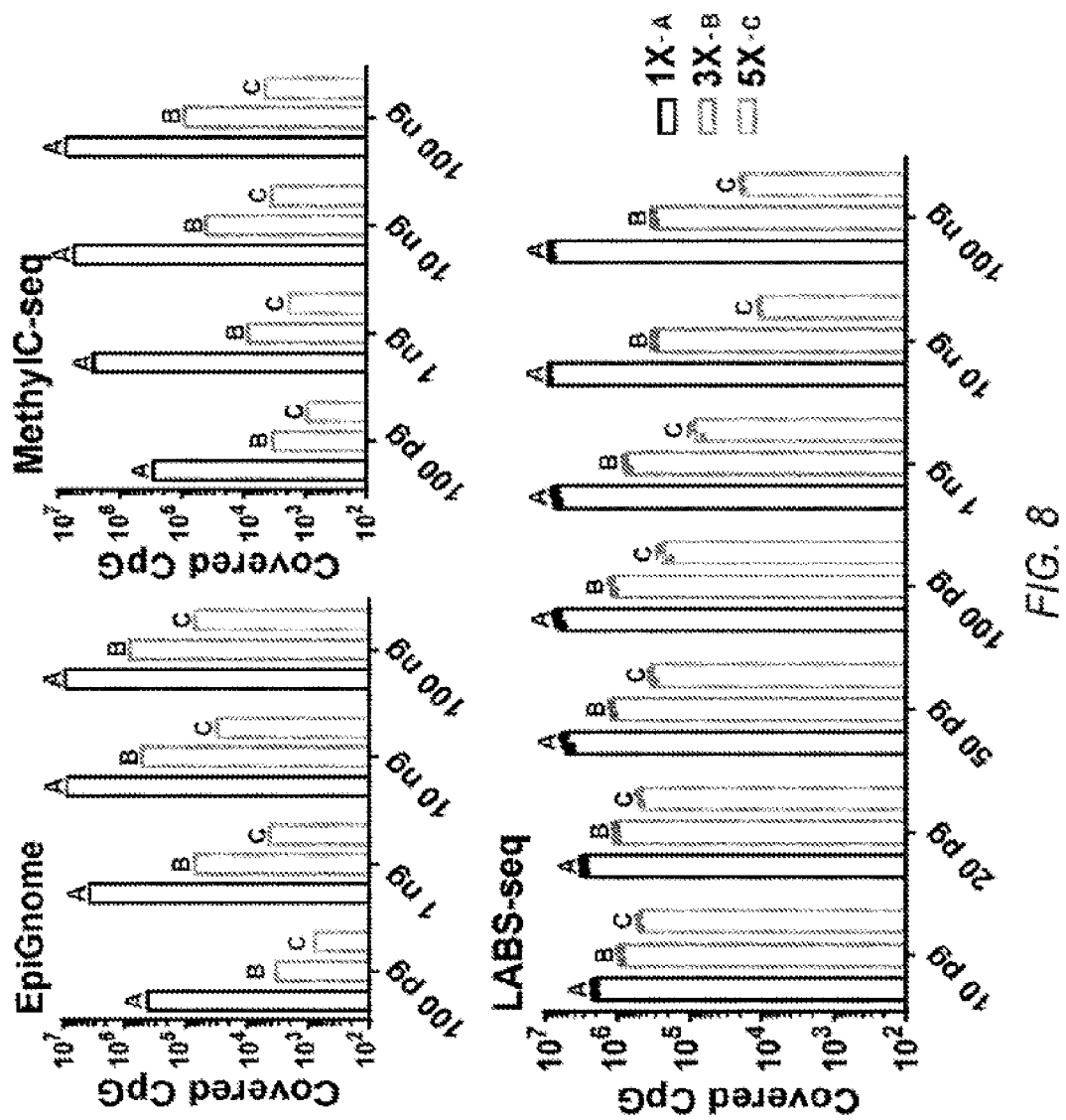
FIG. 8. The covered CpG numbers along increased cutoff reads, 1X, 3X and 5X.

Around 20-40 million single-end reads were obtained per library. The inventors obtained methylated CpGs % on all CpG dinucleotides corresponding to 42.7% of all CpGs in average. Mapping efficiency was 60.3±2.4% for LABS-seq libraries (FIG. 1B), and the ratio didn't drop along with the decreased input materials, even down to 10 pg. More importantly, duplication levels of 1 ng and 100 pg LABS-seq libraries were 7.7±0.5% and 11.3±2.8% respectively, whereas the corresponding levels of EpiGnome and MethylC-seq libraries were extremely high (82.8%-98.5%). To avoid comparison bias from different sequencing depth, the inventors down-sampled 15 million reads for each sample for further analyses. Comparing genome coverage, CpGs coverage, and chromosome coverage, the decrease of coverage along reduced inputs was significantly slow for LABS-seq in contrast to the other methods (FIG. 1C and FIG. 7). In addition, with the increasing number of CpGs sites covered by multiple RNA transcripts (namely multiple reads), IVT amplification acquired more accurate methylation statue of each CpG especially with low input material. In the analysis of 100 pg libraries, LABS-seq obtained at least 300 folds more 5X reads covered CpGs(FIG. 8). Moreover, more CpGs can be achieved by sequencing deeper, as the saturation plots didn't reach a plateau even in 100 pg LABS-seq libraries (FIG. 2A).

Figure 1D:
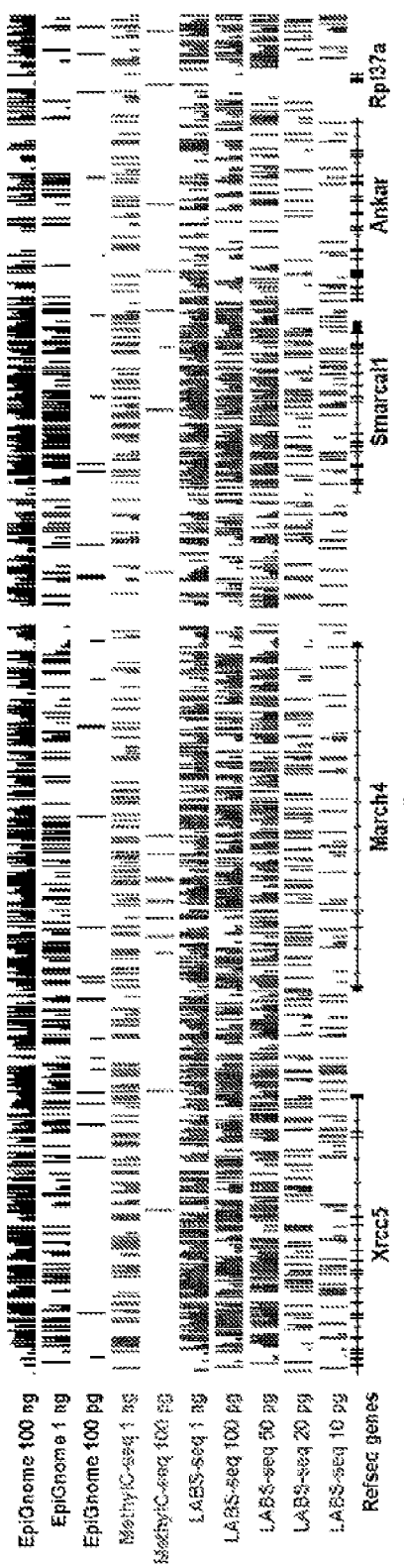
Figure 1E:
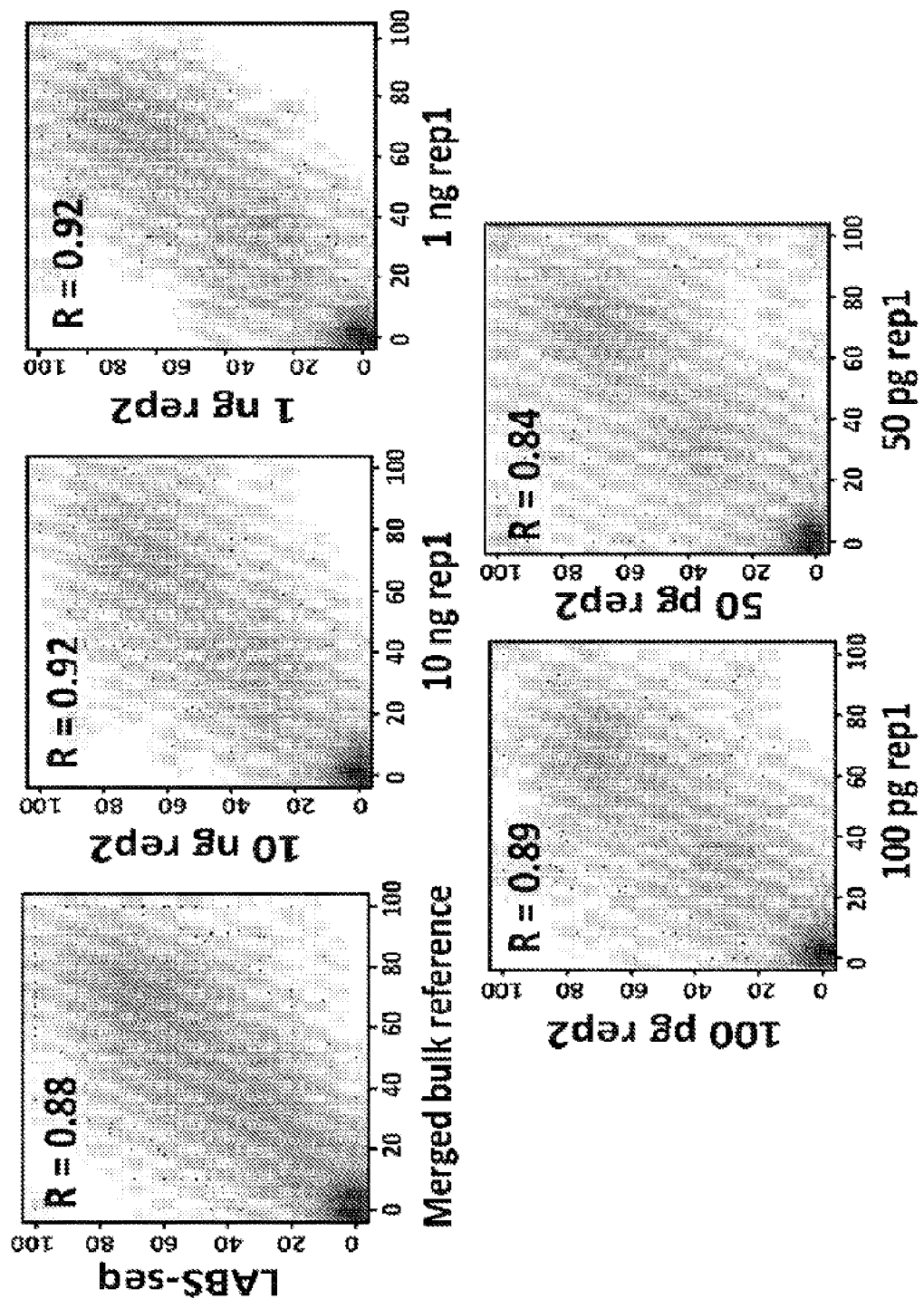

Next, the inventors examined the accuracy of LABS-seq. The global methylation levels of CHG and CHH (0.6-0.9%) indicated that conversion rates were higher than 99% in all LABS-seq libraries. The inventors further merged 100 ng and 10 ng libraries from MethyC-Seq and Epigenome as bulk references and compared with libraries generated with LABS-Seq. A high correlation coefficient (Pearson r=0.88) was observed, indicating the method is highly accurate (FIG. 1E). While there was noticeable coverage deterioration in MethylC-seq and Epigenome libraries with input materials decreasing from 100 ng to 100 pg, LAB S-seq libraries showed similar landscape even with 50 pg input (FIG. 1D). With the libraries from the limited input as 10 pg, the inventors can still identify more CpGs than that presented in 100 pg regular libraries. All these results indicated that LABS-seq could provide sensitive methylome information down to sub-nanogram. The inventors further tested the reproducibility by individual CpGs. High reproducibility between replicates was observed with Pearson r ranging from 0.92 to 0.84. The slightly dropped correlation is due to decreased input DNA materials from 10 ng to 50 pg.

3. Analysis of Sequencing Preference and Uniform Amplification

Sequencing bias in WGBS can come from incomplete BS conversion, PCR amplification and library strategies. The bias may affect accurate estimation of methylation levels and generate distortion of relative differences.' To evaluate the possible sequencing bias, the inventors plotted normalized coverage in genomic bins with different GC content in all three kinds of libraries. Diverse biased GC profiles were observed with two commercial protocols: MethylC-seq and Epigenome libraries showed dramatically increased coverage at AT-rich and GC rich regions respectively, but in lack of presentation at opposite GC rich and AT-rich regions. In contrast, LAB S-seq library displayed less GC bias and moderate coverage in extreme areas (GC<20% and >70%)

Figure 2B:
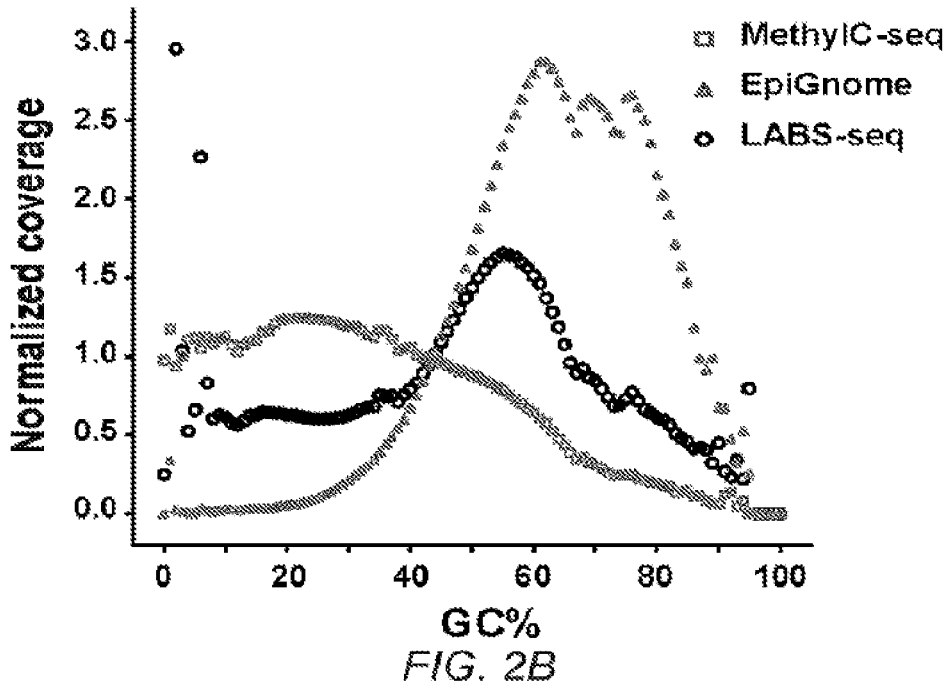

(FIG. 2B), which may benefit from uniform linear amplification of whole genome with little base preference. The inventors also investigated the strands constituents of mapped reads to check if IVT involved strand bias: LABS-seq has similar minus-strands and plus-strands percentages to other two methods, without showing strand bias (FIG. 1B).

Figure 2C:
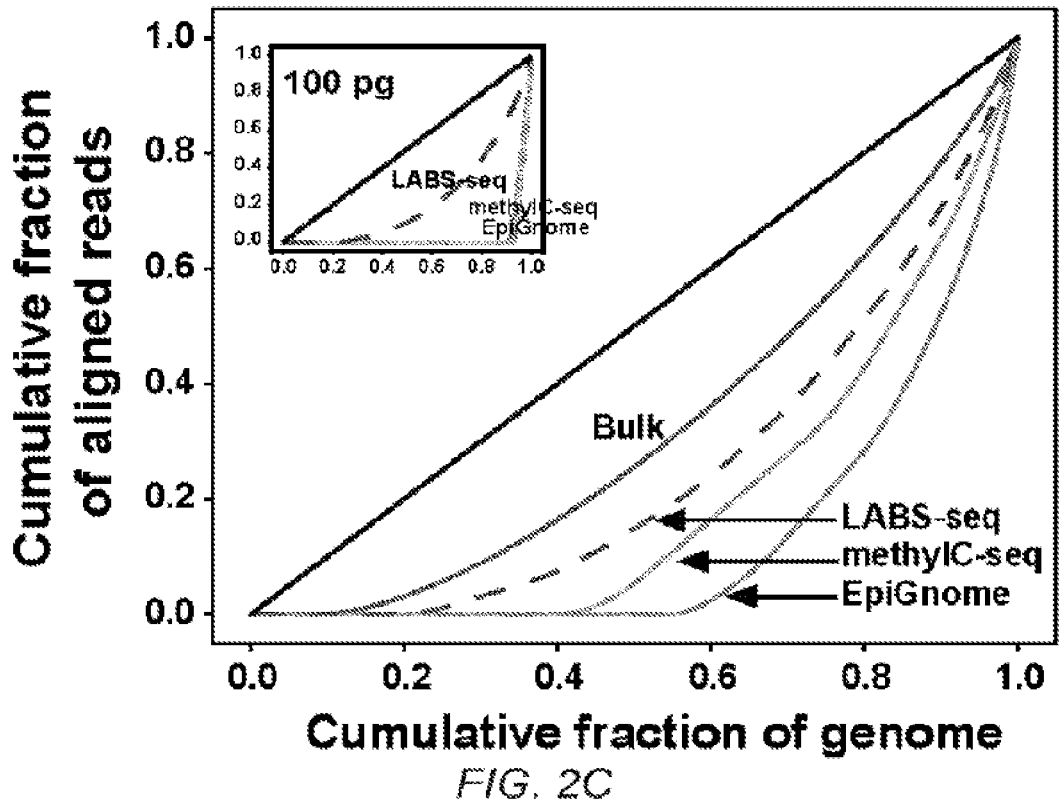

Further, the inventors applied Lorenz curves to evaluate the uniformity of LABS-seq. The black diagonal line represents the perfect coverage uniformity, while a deviation from the ideal diagonal line means a biased reads distribution (FIG. 2C). The inventors compared the curves of bulk, 0.1-1 ng WGBS libraries constructed by LABS-seq and other two pre-BS and post-BS methods respectively. It is evident that LABS-seq performed the best uniformity across the whole genome.

4. Methylation Features of mESCs in LABS-Seq Library

Figure 3A:
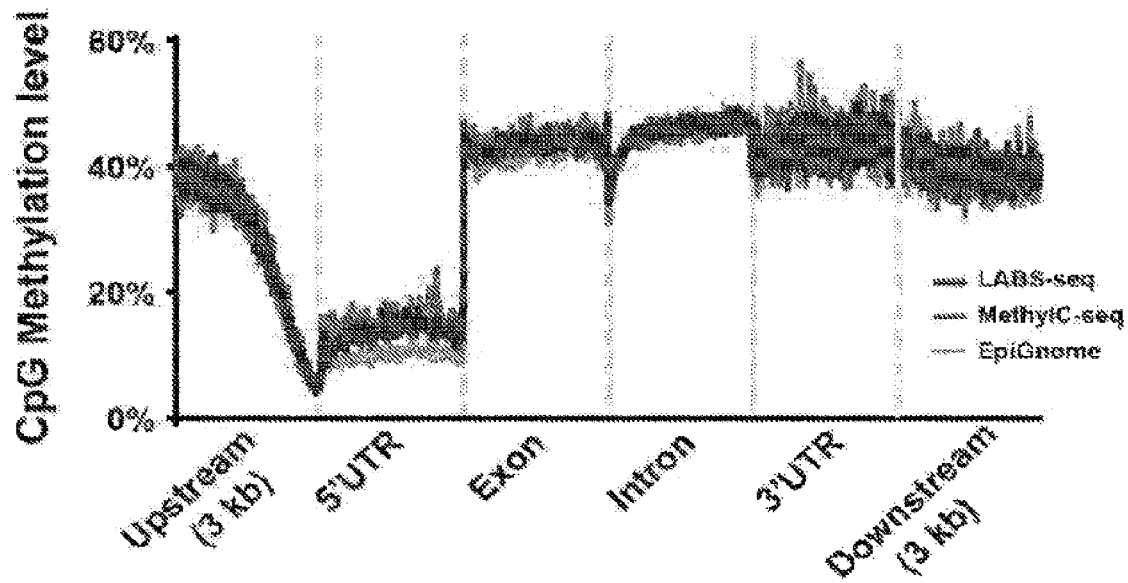
FIGS. 3A-D. (A) Normalized methylated CpG over total CpG residues at annotated genomic loci. (B) Methylation level changes over activating histone mark H3K4me3 and repressed mark H3K27me3. (C) CpGs counts cross different genomic contexts. Each set of bars above each genomic contexts represents, from left to right methyl-seq—1 ng; EpiGnome—1 ng; and LABS-seq—50 pg. (D) The comparison of normalized ChromHMM annotation among three WGBS methods. Each set of bars above to the right of the ChromHMM states represents, from top to bottom methyl-seq—1 ng; EpiGnome—1 ng; and LABS-seq—50 pg.
Figure 3B:
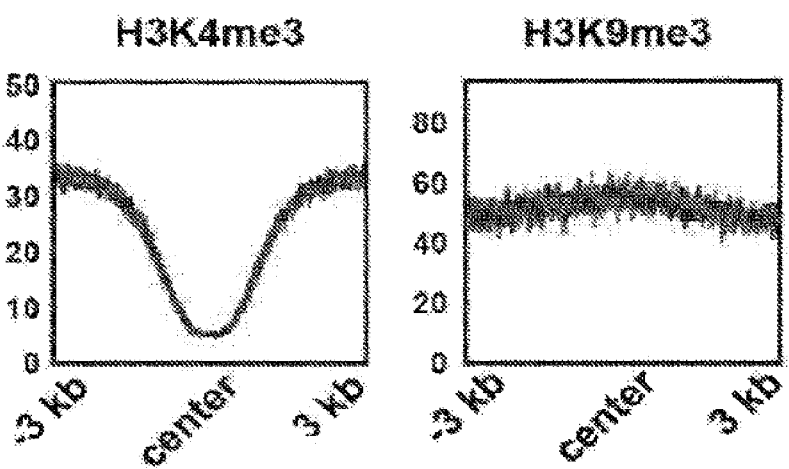
Figure 3C:
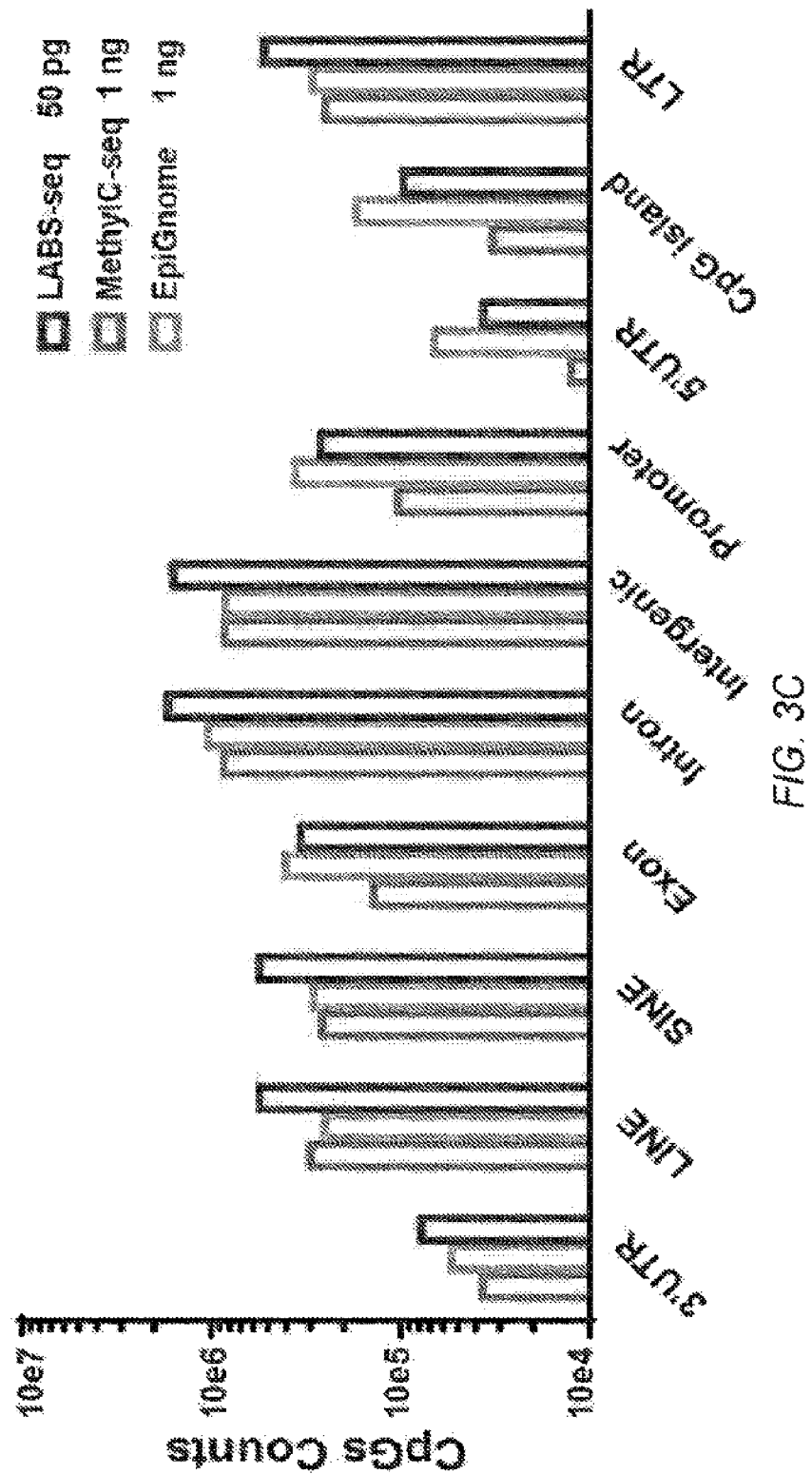
Figure 3D:
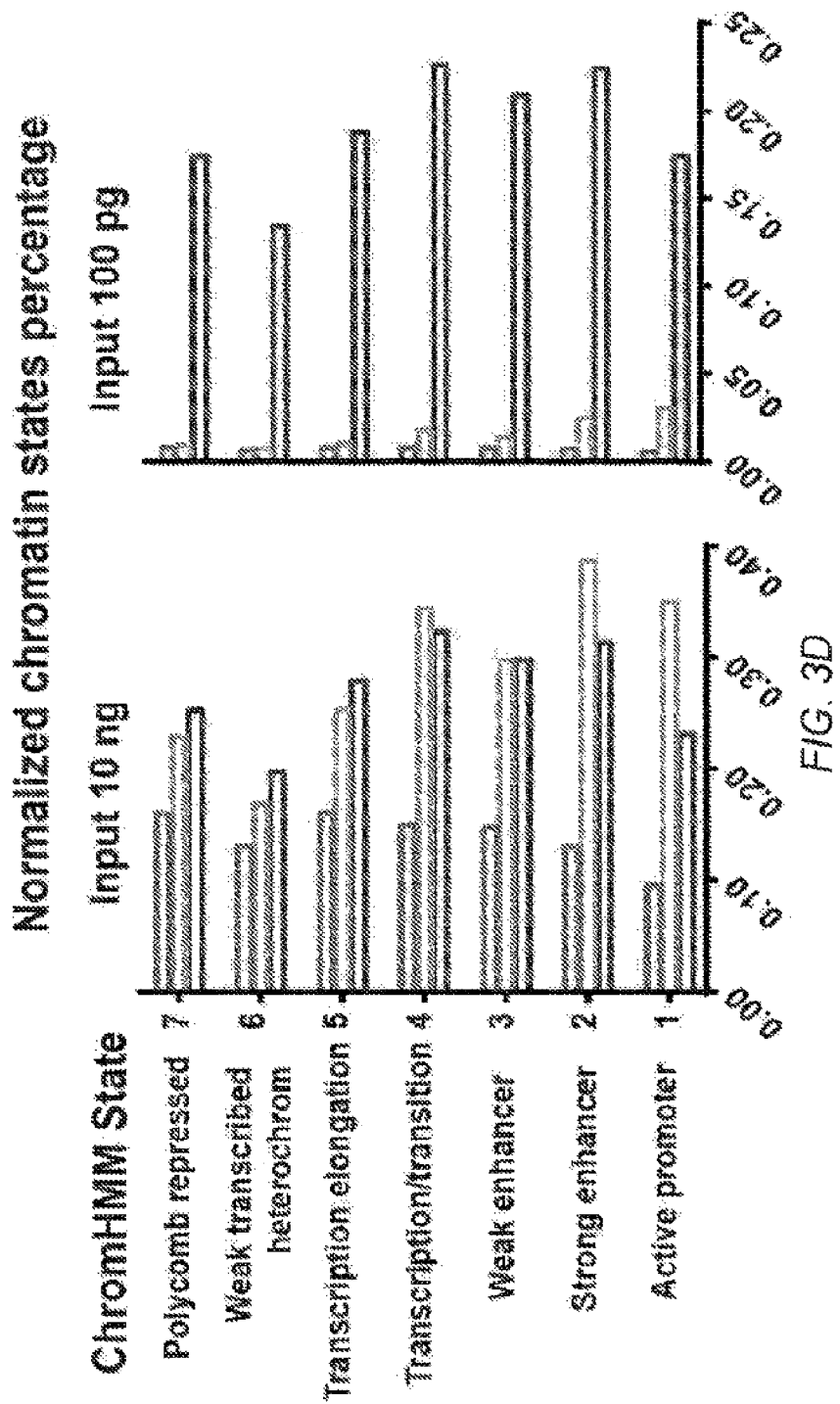
Figure 9:
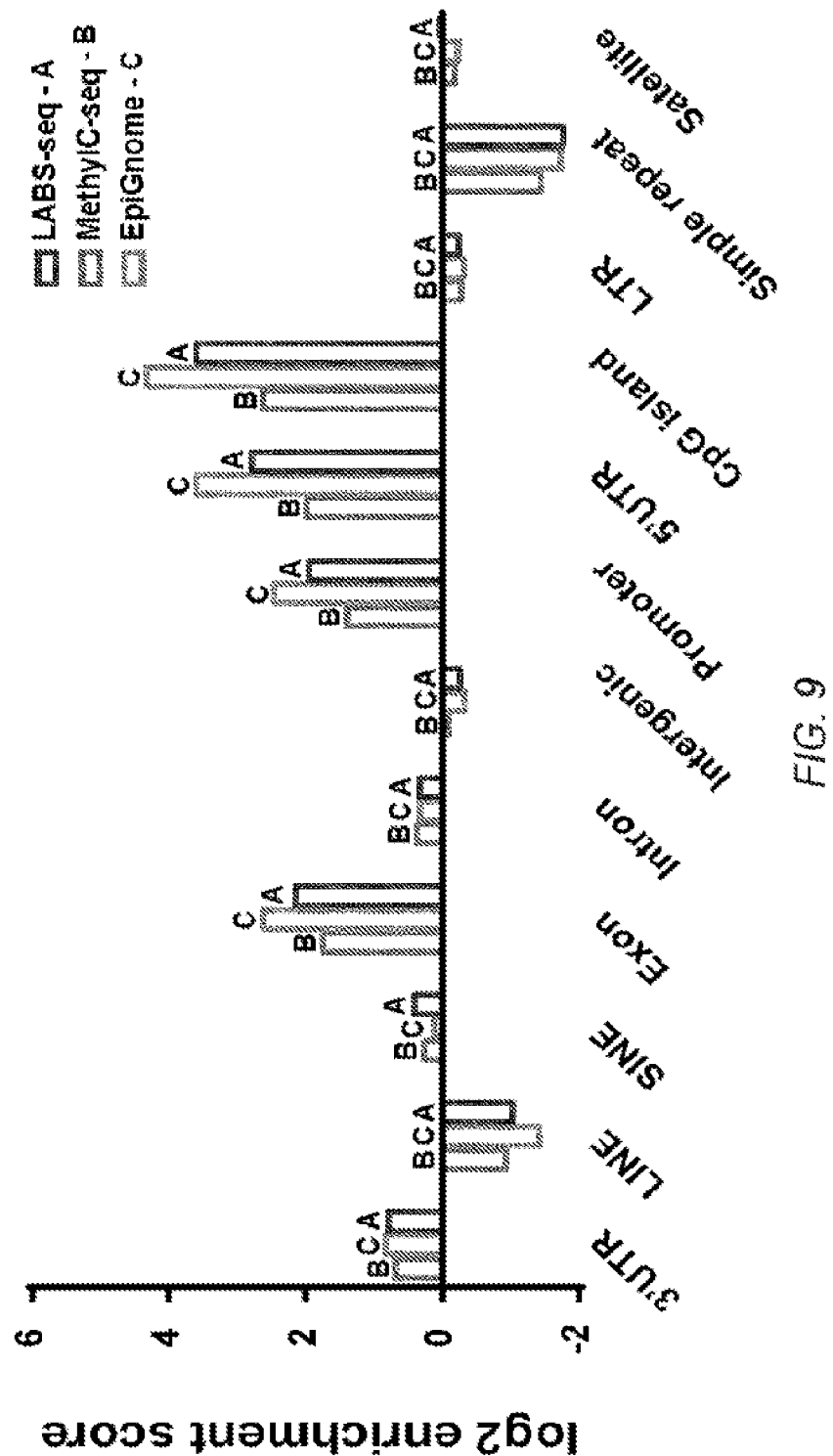
FIG. 9. CpGs log 2 enrichment score cross different genomic contexts: 3'UTR, LINE, SINE, Exon, Intron, intergenic, promoter, 5'UTR, CpG Island, LTR, simple repeat and satellite.

Features of the methylome from the libraries under the three protocols were almost identical in varied aspects. The inventors first drew methylation density over various genomic features presented by the three methods (FIG. 3A). The inventors observed a significant decrease from 3 kb upstream to transcriptional start site (TSS) followed by local depletion of methylation at 5'UTR region, and the density returned to the similar level of upstream 3 kb (~40%) at exon, intron, 3'UTR and downstream regions. In addition, consistently, the inventors found a marked decline in methylation at activating histone mark H3K4me3 and an increase at repressive mark H3K9me3 by checking the methylation rate over different histone modification characteristics (FIG. 3B). The inventors then investigated CpGs counts cross different genomic contexts (FIG. 3C), which also showed excellent agreements among the three methods. Yet tit was noticed that the 50 pg LABS-seq library showed similar or even better coverages of each context than the others using 20 folds amounts of gDNA materials. The normalized reads of above contexts were further illustrated by log 2 enrichment score (FIG. 9), where the three protocols showed concordant preference in 3'UTR, Exon, promoter, 5'UTR and CpG Island regions. The inventors also used ChromHMM chromatin states across the genome to quantify different coverage bias of the three methods. EpiGenome method preferred to annotate to state 1, 2 and 4 (active promoter, strong enhancer, and transcription/transition respectively), while LABS-seq has state 2 and 4 preference. When the input material dropped to 100 pg, LABS-seq library remained comparable tendency among different states, and provided more annotative information than Epigenome and MethylC-seq.

5. Genome-Wide Mapping of 5mC in cfDNA Using LABS-Seq

Figure 4A:
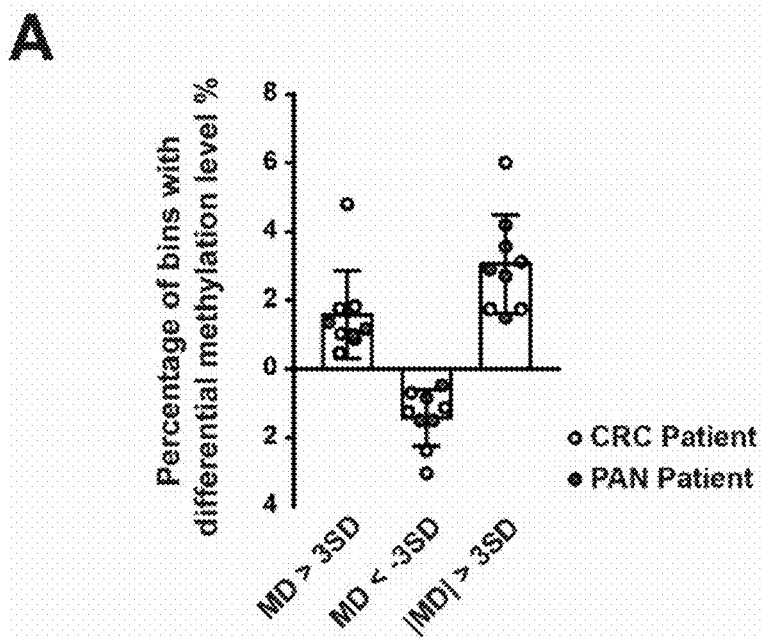
FIGS. 4A-B. (A) Percentage of bins showing hypomethylation(|MD|<|−3 SD), hypermethylation (MD>3 SD), and differential methylation(|MD|>3 SD) in CRC patients and PAN patients. (C) Methylation analyses for one health control, one CRC patient and one pancreatic cancer patient. The methylation z scores of the three samples were located from the outer to the inner ring.
Figure 4B:
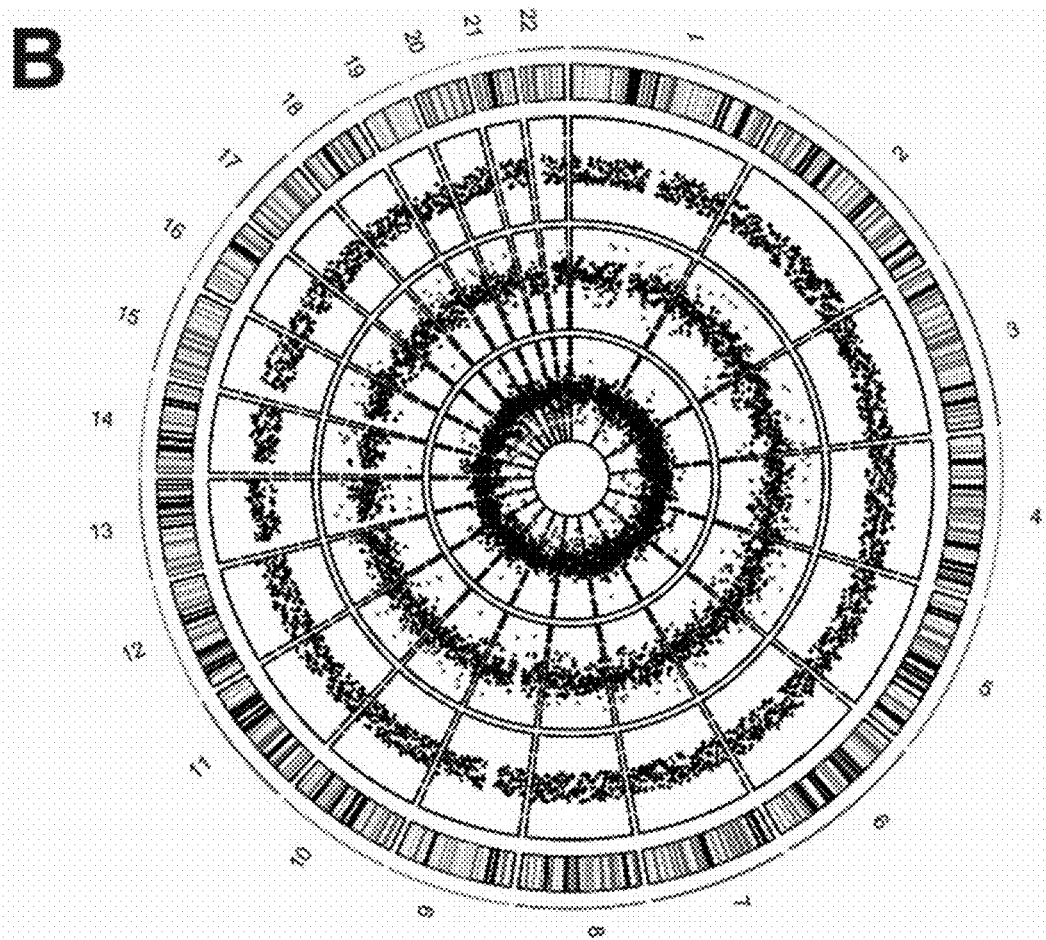
Figure 10:
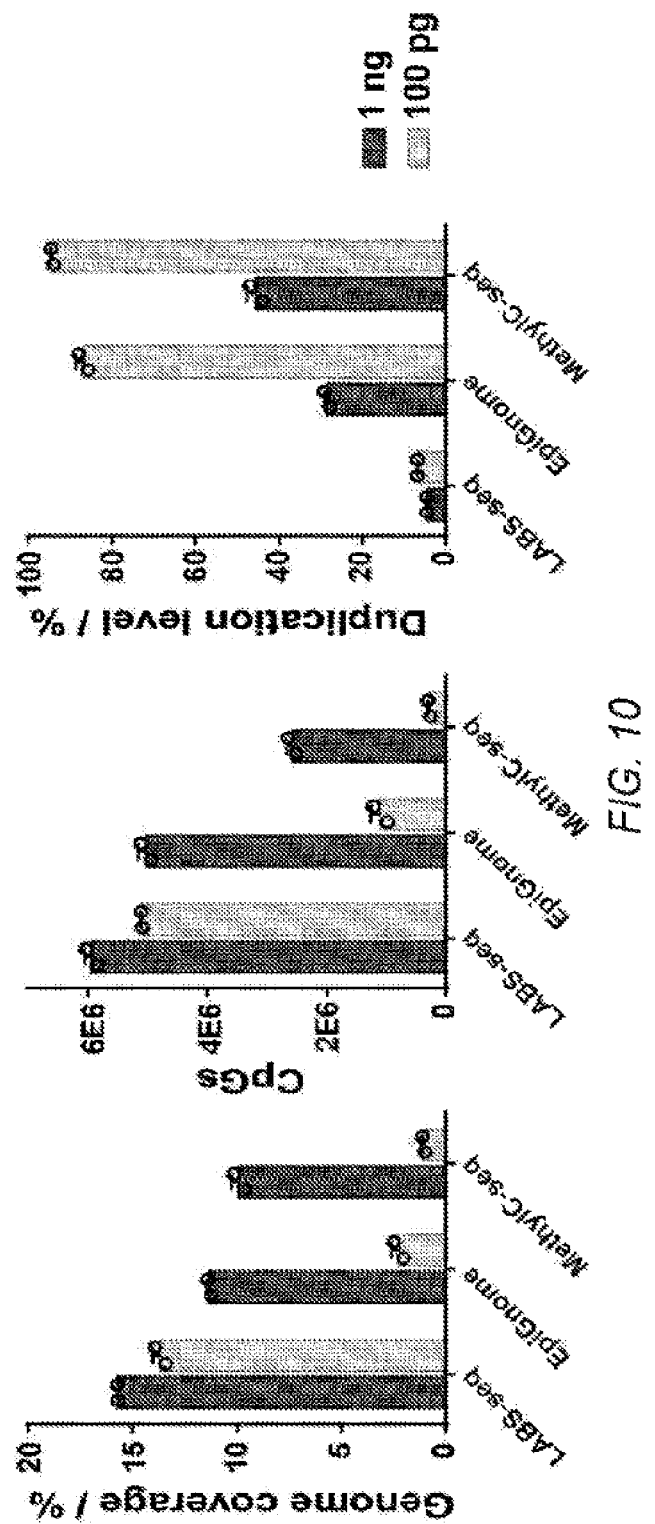
FIG. 10. cfDNA LABS-seq libraries comparison (A) Genome coverage (B) CpGs numbers (C) duplication level comparison among LABS-seq, MethylC-seq and EpiGnome. All these cfDNA libraries were constructed by 100 pg and 1 ng cancer-free cfDNA with technical replicates. Each point is a library.

As the LABS-seq performed excellently in library construction from limited inputs, the inventors tested LABS-seq on pooled cancer-free plasma cfDNA. Epignome and MethylC-seq protocol were compared as above (FIG. 10). LABS-seq showed overwhelming advantages in genome coverage, CpGs coverage, and duplication level. Then the inventors applied this method to patient cfDNA samples. 15 patients were involved, including 6 healthy, 6 Colon cancer and 3 Pancreatic cancer patients 6. Genome-Wide Hypo-/Hyper-Methylation for Cancer cfDNA Genome-wide hypo-/hyper-methylation was investigated since global methylation alteration was discovered in many cancer types. The inventors checked methylation density (MD) in each 1-Mb bin of whole genome5 (2734 bins in total with sex chromosomes excluded). All healthy individuals showed relatively stable levels in each bin, while CRC and PAN cancer plasmas displayed high variation among the corresponding bins. The numbers of bins with MD>3 SDs varied from the mean of healthy cfDNA were 177±83.6 and 108±19.2 respectively in CRC and PAN cfDNA. The inventors determined the percentage of high variation features of patients' cfDNA (FIG. 4A). The annotation of these high variation features showed that most of them were located at intergenic and intronic regions, while it also displayed high enrichment in promoters. Functional enrichment analysis identified that paraxial mesenchyme was highly enriched in CRC-derived hypo-/hyper-methylated bins (FDR=5.36e-6), which agrees with the important roles of mesenchymal cells in colon cancer. If recruiting more samples, the inventors could effectively distinguish cancer patients based on genome-wide hypo-/hyper-methylation with relatively low sequencing depth.

7. DMRs as Classification Biomarkers

Figure 5A:
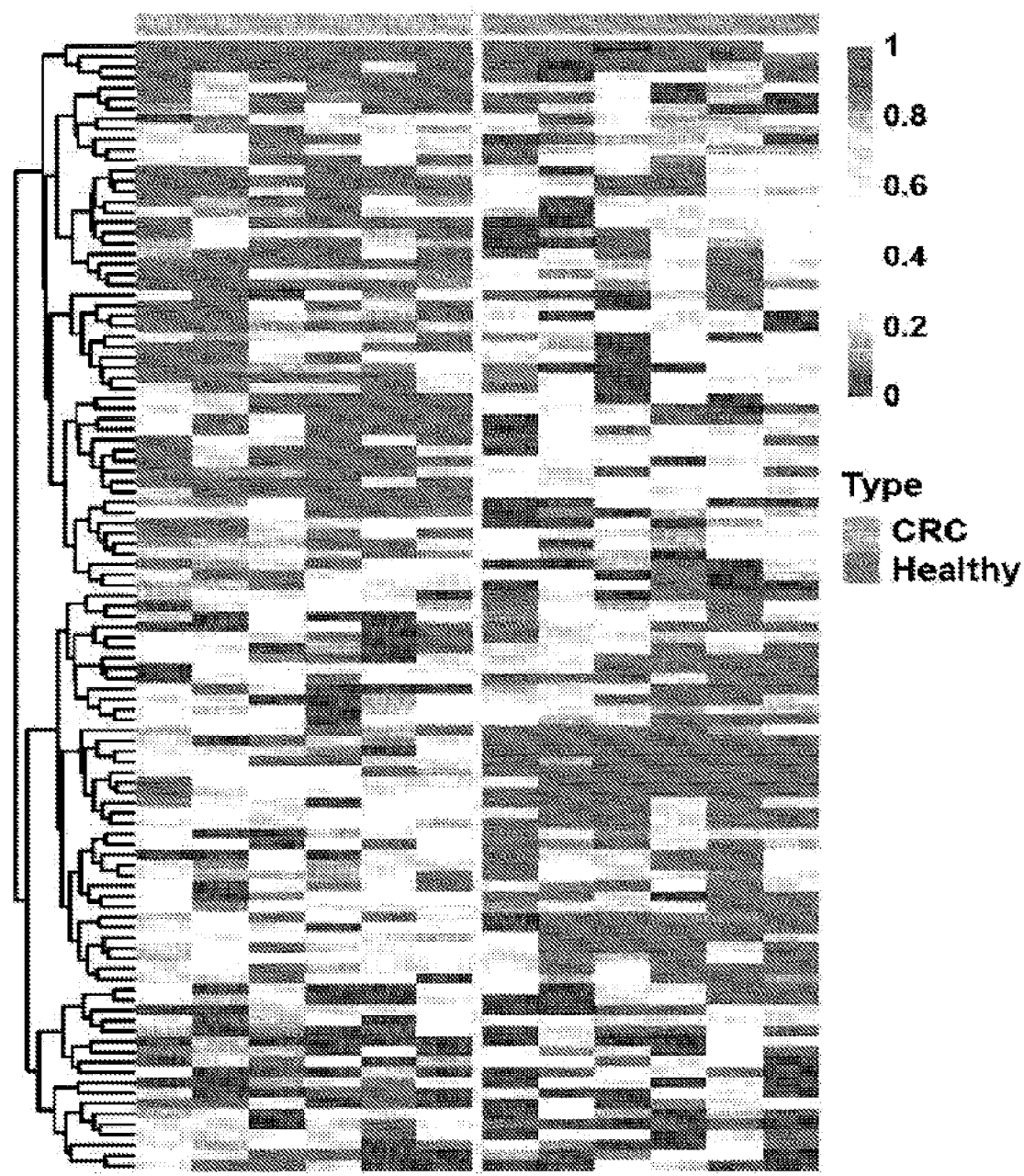
FIGS. 5A-D. cfDNA DMRs for grouping CRC patients and Healthy individuals (A) Heatmap of 109 DMRs in CRC patients and healthy controls. DMRs and samples were clustered by Euclidean distance. (B) Genome-wide distributions of DMRs. (C) hierarchical clustering of CRC group and Healthy group (D) PCA plot of all CRC patients and Healthy individuals.
Figure 5B:
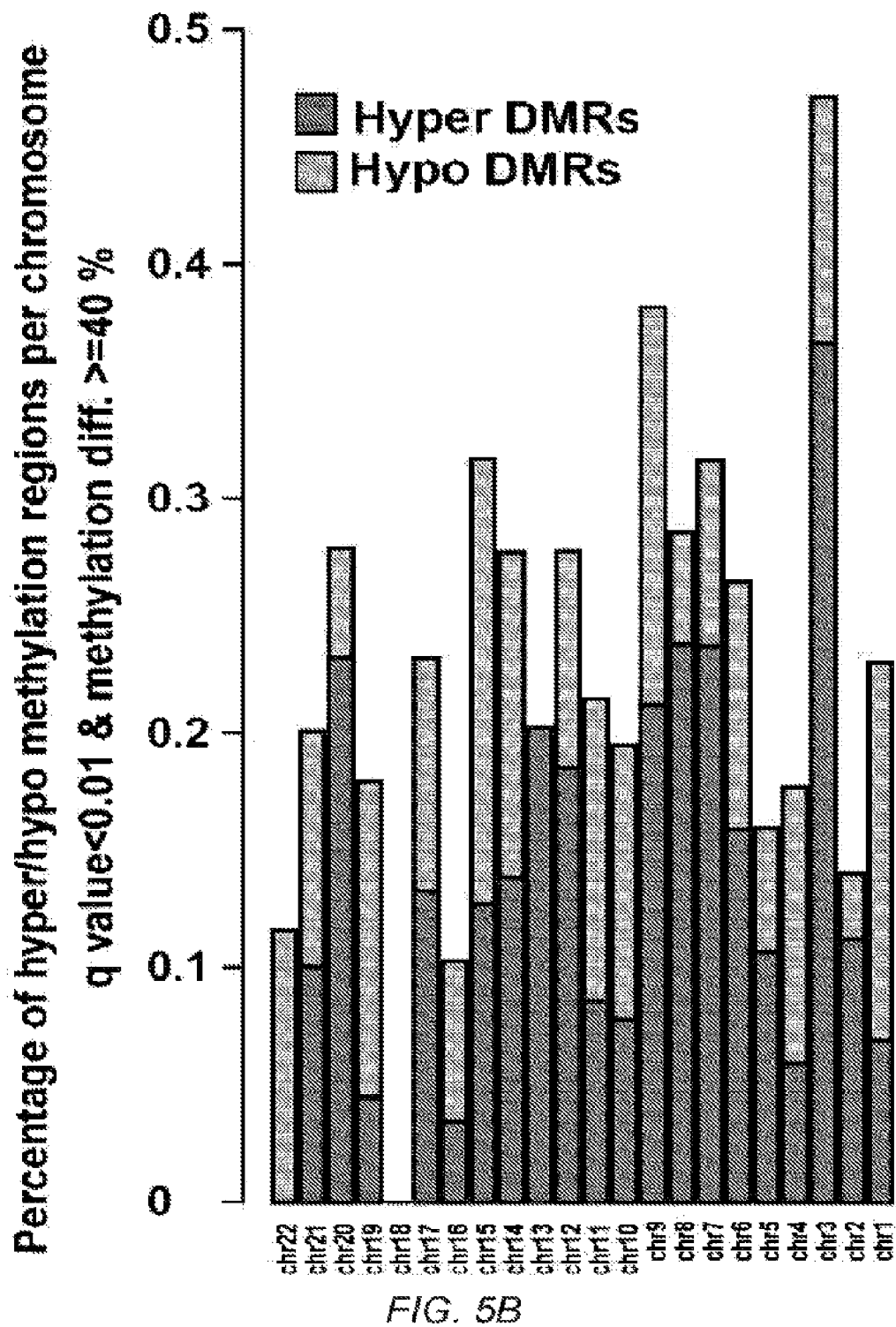

To examine whether LABS-Seq data can lead to the discovery of differentially methylated regions (DMRs), the inventors compared different patient groups using 1-kb bins and found 109 were significantly differentially methylated between CRC and healthy patients (FIG. 5A). These DMRs were distributed to whole genome (FIG. 5B, excluding sex chromosome and mitochondria). Among them, 47 DMRs were hypo-methylated in CRC groups, and with 62 DMRs were hyper-methylated. The inventors further observed that the CRC-specific hypo-methylated DMRs were particularly enriched in repeat regions such as LINE and SINE while the CRC-specific hyper-DMRs were enriched in promoter and exon regions which correlated with the regulation of gene expression, indicating that the difference of 5mC profiles between healthy and CRC patients is substantial where may reveal cancer related biological functions. All these results suggest that the method can give robust 5mC genomic profiling and disclose reasonable 5mC differences between patient groups.

Figure 5C:
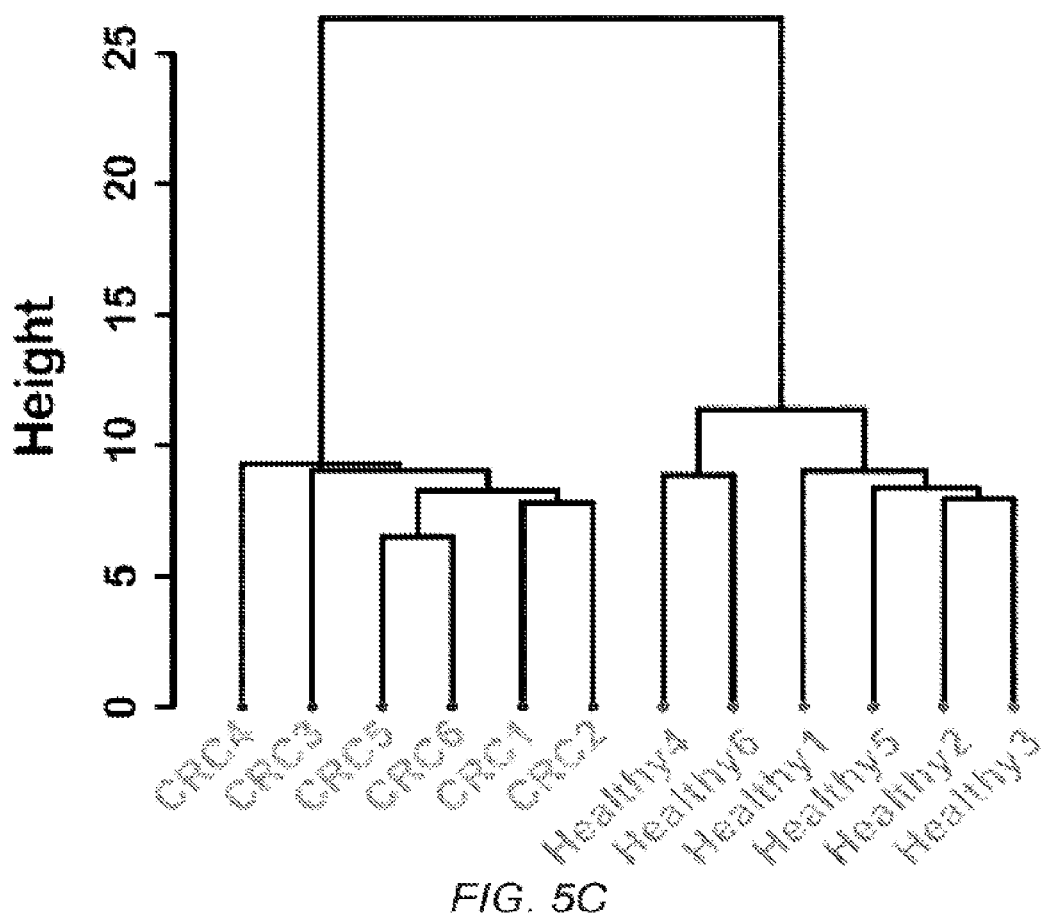
Figure 5D:
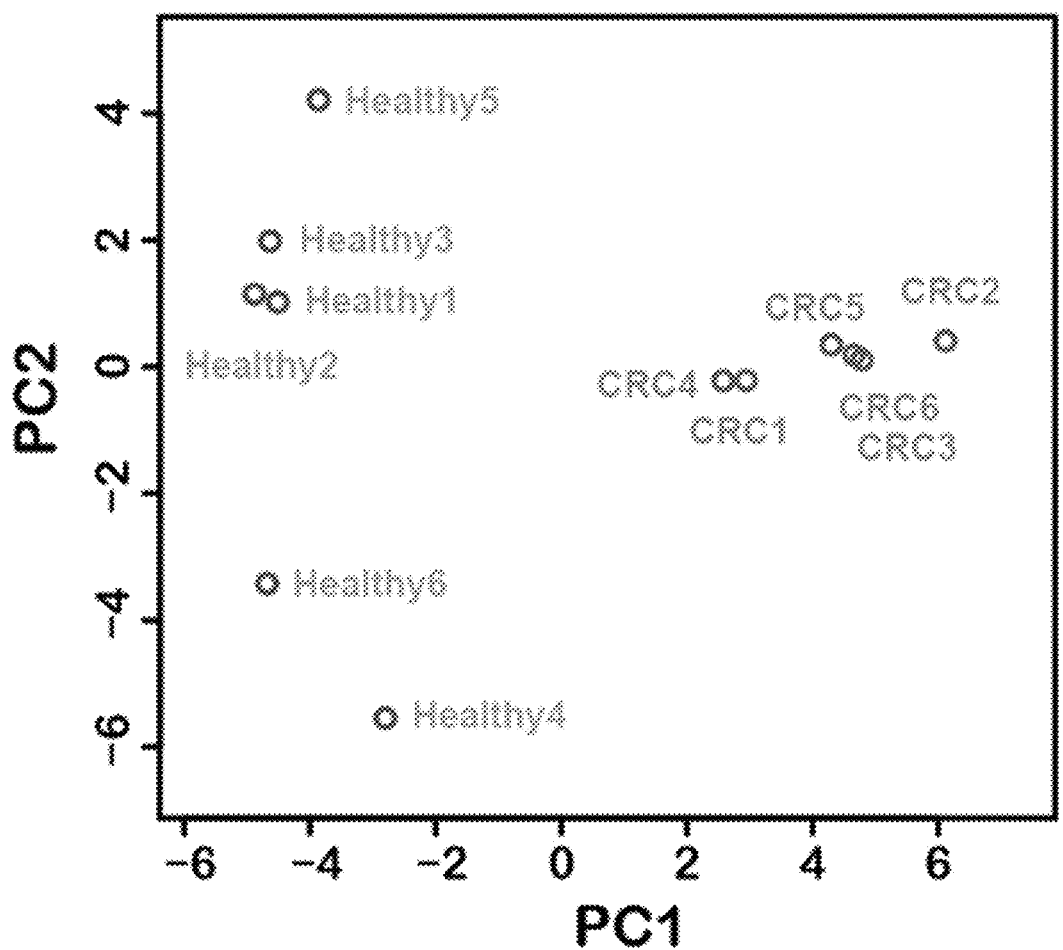

To further evaluate the classification effects of these DMRs, the inventors clustered the features in different groups using hierarchical clustering (FIG. 5C). Two patient groups can be directly and fully separated by unsupervised clustering in a both sensitive (6/6 CRC) and specific (6/6 Healthy) manner. The inventors also performed PCA analysis on DMR features and noticed that different patients could be readily grouped based on disease classification (FIG. 5D). Among the DMRs between CRC and healthy group, the inventors acquired some potential CRC marker genes, such as CCR9 (chemokine receptor 9, correlating with CRC invasion and metastasis), BRD4 (bromodomain-containing protein 4, which frequently be aberrantly methylated in colon cancer), LGAL9 (a tumor suppressor gene hyper-methylated in CRC patients), and IRF1 (a known tumor suppressor in multiple carcinomas and can induce tumor cell apoptosis).

CEA (carcinoembryonic antigen)21 is a clinically useful CRC blood marker (ref range 0-3.4 ng/mL). The CEA serum test results of patient CRC 5, CRC 4 and CRC 6 were 1.7 ng/mL, 4.5 ng/mL and 88.2 ng/mL respectively. In DMRs clustering and PCA, the three patients were all naturally classified as cancer. It suggested DMRs markers found by LABS-seq method could be a kind of much more sensitive indicator than CEA or other protein serum marker. CRC 1 is an SSA/polyp patient, which is a high-risk precancerous lesion, and CRC 1 was grouped into CRC group. It showed the possibility to apply 5mC cfDNA in early screening for the high-risk precancerous lesion. If having more precancerous/cancer in process patients, the inventors could get 5mC markers respectively for premalignant disease and cancer.

8. Tissue-of-Origin Deconvolution cfDNA could be considered as a mixture of DNA derived from different tissues and plenty of hematopoietic cells. Although different tissue types actually have the same DNA sequence, 5mC methylation profiles are highly tissue-specific.[14] Using tissue-specific 5mC features which displayed negligible or minor proportion in other tissues, the inventors can get the mixing proportions of different tissues by deconvolution algorithms, trace the tissue-of-origin, and has the potential to predict specific cancers. 10,13,22

Figure 6A:
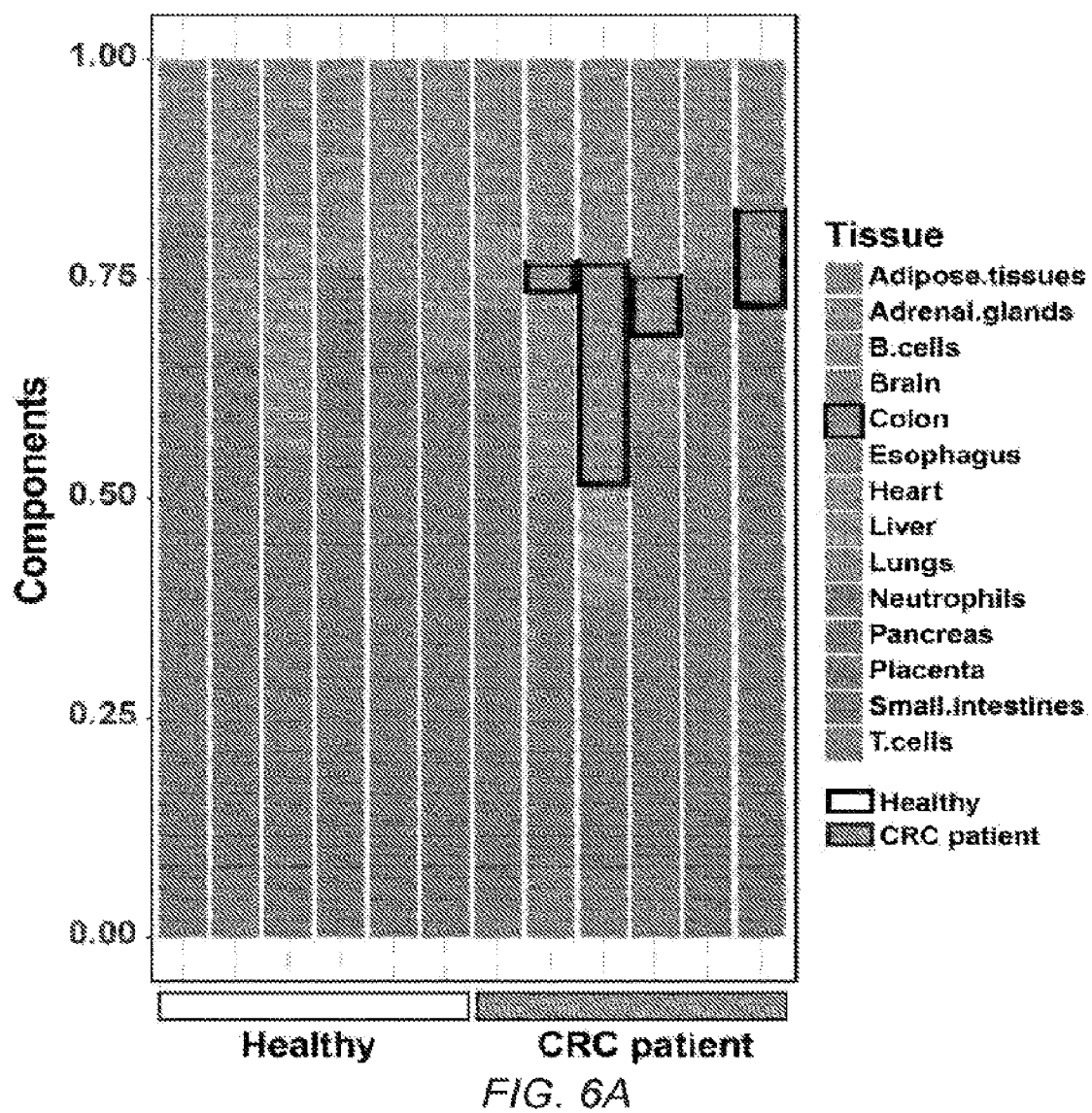

In this way, the inventors reanalyzed the public WGBS data from 14 tissues generated by Roadmap project (found on the world wide web at genboree.org/epigenomeatlas/index.rhtml) and another two studies.[23, 24] Totally 5823 significant DMRs were found by comparing one of the tissues to the rest. These DMRs were then used as markers for deconvolution. As a proof-of-concept, the inventors found neutrophils took the most considerable part of almost all cfDNA samples (FIG. 6A, 45-68% in healthy; 20-62% in CRC), which is consistent with former studies. 22 The inventors noticed that the neutrophils percentage in CRC group showed a significant decline along with an increased contribution from colon (FIG. 6C). Four CRC patients (4/6) had 3.1% to 25% colon tissue proportions in cfDNA (FIG. 6B), whereas the contributions in healthy group were undetectable. The result supported the concept of using DNA methylation features for cancer type prediction. By combining genome-wide hyper-/hypo-methylation detection with tissue-of-origin deconvolution, the inventors can not only detect cancer but also predict the location of solid tumor.

B. Discussion

LAB S-seq is the first whole genome amplification based WGBS-seq method for liquid biopsy. Using LABS-seq technique, the inventors took a comprehensive exploration of signatures in colon cancer patients. The patients displayed significant DNA methylation aberrant in plasma cfDNA comparing to healthy individuals. Even though only 6/6 CRC/healthy patients were involved in DMRs unsupervised clustering and marker identification, the inventors got finer markers like CCR9 and BRD4 and an entirely confident clustering. In CRC, the inventors found a precancerous sample was classified into the CRC group. It suggested that cfDNA DNA methylation may be useful in early screening, in particular in the precancerous lesion which is not big enough to be detected or indeterminate in imaging. Since cfDNA is an equilibrium of DNA fragments from different sources, it is able to provide the whole DNA methylation picture of human body. Most importantly, different types of cancers display quite diversed methylation signatures, and thus one can realize tissue-of-origin prediction and enhance solid-tumor detection based on the detection of methylation features. In future works, to take full advantages of LAB S-seq, one can exploit into longitudinal monitoring to assist tumor treatment, distinct cfDNA signatures towards primary solid tumor and metastatic lesion.

Besides blood, the technique can work on including but not limited to urine, cerebrospinal fluid (CSF) and aqueous humour cfDNA, which are reported with smaller DNA fragments size or lower concentrations than those in the blood. LABS-seq is applicable to single cell study as well. After single cell gDNA fragmentation using transposase or nucleases etc., the technique could be performed to amplify several picogram material to nanogram. It provides investigators a powerful and accurate tool to look at epigenetic alterations across whole genome in circulating tumor cell, cellular heterogeneity and embryo with in-depth understanding of cancer and embryonic development.

C. Methods

1. Patient Recruitment and Plasma Samples

A total of 6 patients with colon cancer, 3 pancreatic cancer, 6 healthy individuals were recruited in the study.

Blood from patients with colon cancer were collected prior to resection of the malignant lesion. The diagnosis was confirmed by surgical pathology after resection of the lesion. Blood from patients with pancreatic cancer. Healthy individuals were patients who underwent routine health examination with no malignant or pre-malignant diseases found.

Blood from healthy individuals were collected at time of the procedure. Blood samples were collected in streck tubes and were centrifuged for 1,350 g for 12 min at 4° C. twice, and 13,500 g for 5 min at 4° C. CfDNA was isolated from 0.1-1 mL plasma using QIAamp Circulating Nucleic Acid Kit (Qiagen, 55114).

2. Cell Culture and Genomic DNA Isolation mESC cells were grown on gelatin coated plates in Dulbecco's Modified Eagle Medium (DMEM) (Invitrogen Cat. No. 11995) supplemented with 15 FBS (Gibco), 2 mM L-glutamine (Gibco), lx nonessential amino acids (Gibco), 1% penicillin/streptavidin (Gibco), 1Xβ-mercaptoethanol (Sigma), 1000 u/mL leukemia inhibitory factor (Millipore Cat. No. ESG1107), 1 µM PD0325901 (Stemgent, dissolved in DMSO), and 3 µM CHIR99021 (Stemgent, dissolved in DMSO). All cells were cultured at 37° C. under 5.0% $CO_2$ and passaged every 2 days.

For genomic DNA isolation, cells were harvested by centrifugation for 3 min at 1000×g. DNA was extracted by AllPrep DNA/RNA Mini Kit from Qiagen according to protocol.

3. Preparation of T7 Adaptor

Oligonucleotides were purchased from IDT with HPLC purification. T7 sequence/5Phos/iMe-dC/iMe-dC/iMe-dC/TATAGTGAGT/iMe-dC/GTATTAATTT/iMe-dC/G/iMe-dC/GGGG/iMe-dC/T (SEQ ID NO:4) iMe-dC refers to internal 5-Methyl deoxyCytidine and short helper CGACT-CACTATAGGGT/3Phos/(SEQ ID NO:5) was dissolved in annealing buffer (10 mM Tris-HCl pH 8.0, 0.1 mM EDTA, 50 mM NaCl). The T7 adaptor were prepared by mixing the two oligos equally to 50 µM and annealed using PCR machine (95° C. 5 min, −0.25° C./min cooling down to 4° C.). The adaptor was diluted to 15 µM by annealing buffer and stored at −20° C.

4. Bisulfite Conversion

Bisulfite treatment was carried out by MethylCodeTM Bisulfite Conversion Kit (Invitrogen, MECOV50). Briefly, 20 µL gDNA or cfDNA was mixed with 130 µL CT conversion buffer, and incubated at 98° C. 10 min, 64° C. 2.5 hr, 4° C. hold. The converted DNA was purified by spin column provided in the kit with an on-column desulfionation and eluted in 9-20 µL preheated (55° C.) Nulease-free H2O (Ambion, AM9937).

5. Methyl C-Seq Whole Genome Bisulfite Sequencing mESC gDNA were fragmented into 150-400 bp dsDNA fragments. Sequencing libraries were prepared by using NEXTflex® Bisulfite Sequencing Kit (PerkinElmer) according to manufacturer's protocol. Briefly, after end repair and 3'-adenylation reaction, methylated adaptor was ligated to two ends of DNA fragments. Then, DNA was subjected to bisulfite conversion. Finally, the library was amplified by KAPA Hifi Uracil Plus Polymerase (Kapa Biosystems) and purified by 0.8X AMPure XP beads twice. The library was subjected to NextSeq 500 SR80.

6. Epignome Whole Genome Bisulfite Sequencing

TruSeq DNA Methylation Kit was used. GDNA or cfDNA was subjected to bisulfite conversion at first. Synthesis random primers were annealed to converted ssDNA and following manufacturer's protocol. DNA strands containing a specific sequence tag from random primers were synthesized. Then, added known sequence tag to the 3'-end of DNA strands. The di-tagged DNA was purified by using 1.6X AMPure XP beads. The library was amplified by Failsafe PCR enzyme system and cleaned up with 1.0X AMPure XP beads. The library was sequenced by NextSeq 500 SR80.

7. Whole Genome LABS-Seq

CfDNA or fragmented gDNA was ligated with T7 adaptor using KAPA Hyper Prep Kit (KAPA BIOSYSTEMS, KK8502). Briefly, DNA in 10 μL Nulease-free H2O was mixed with 1.4 μL End Repair & A-Tailing Buffer and 0.6 μL End Repair & A-Tailing Enzyme Mix, incubated at 20° C. 30 min, 65° C. 30 min. Next, 1 μL homemade T7 adaptor, 1 μL H2O, 6 μL Ligation Buffer and 2 μL DNA Ligase were added and incubated at 20° C. for 4 hours or 4° C. overnight. After post-ligation clean-up using 1.4X AMPure XP Beads, it was subjected to bisulfite treatment. Bisulfite converted DNA in 10 uL H2O was mixed with 3 μL 5X EpiMark Buffer, 0.3 μL 10 μM T7 Primer (AGCCCGCGAAAT-TAATACGACTCACTATAGGG (SEQ ID NO:3), IDT with HPLC purification), 0.3 μL 10 mM dNTP(NEB, $N_{04475}$), 0.3 μL EpiMark Hot Start Taq DNA Polymerase (NEB, M0490S) and 1.1 μL Nuclease-free H2O. T7 primer annealing and extension were performed by 95° C. 60 sec, 59° C. 60 sec, 68° C. 5 min, 4° C. hold. Then, 1 μL 0.85 mg/mL QIAGEN protease was added and incubated at 50° C. for 2 hours, followed by heat inactivation at 75° C. 30 min. The T7 tagged dsDNA fragments were diluted with 22 μL H2O and mixed with 60 μL T7 reaction pre-mixture (NEB HiScribe™ T7 High Yield RNA Synthesis Kit E2040S, lx T7 Reaction Buffer, 10 μL RNA polymerase Mix, 10 mM ATP/GTP/UTP/CTP) and 0.4U/μL SUPERase In RNase Inhibitor (Life Technologies, AM2694). The reaction was incubated at 37° C. for 12-16 hours.

After overnight T7 in vitro transcription, DNase I and digestion buffer was added to digest DNA templates at room temperature for 20 min. Then RNA transcripts were purified by RNA Clean&Concentrator kit (Zymo Research, R1013) and eluted in 15 μL H2O. RNA yield was quantified by Qubit 2.0 RNA HS Assay Kit (Life Technologies, Q32855). At most 100 ng RNA was used for library construction (KAPA BIOSYSTEMS, KAPA RNA HyperPrep kit, KK8540). Followed the manufacturer's protocol, RNA in 10 μL H2O was mixed with 10 μL 2X Fragment, Prime and Elute Buffer. The reaction was heated at 65° C. for 1 min and quenched on ice. 1st strand synthesis was initiated by adding 10 μL master mix(buffer and KAPA Script enzyme) and performed at 25° C. 10 min, 42° C. 15 min, 70° C. 15 min, 4° C. hold. 30 μL 2nd strand synthesis and A-tailing mixture was added to the reaction and incubated at 16° C. 30 min, 62° C. 10 min, 4° C. hold. Then, illumina adaptors were ligated at 20° C. for 15 min. After two rounds of post-ligation clean-up using KAPA Pure Beads, the elution was PCR amplified (45 sec at 98° C.; 10-12 cycles of 15 sec at 98° C., 30 sec at 60° C., 30 sec at 72° C.; 1 min at 72° C.) and purified by 1X Ampure XP Beads. Finally, the library was sequenced using NextSeq 500 SR80 platform.

8. Data Processing and Analysis

Raw sequencing reads were first trimmed to remove sequencing adaptors and low-quality nucleotides by Trim Galore. Bismark were then used to map trimmed reads to mm9 and hg19 reference genomes, respectively. Further duplication removal and mC calling were conducted by wrapper scripts in Bismark package. Cytosine residues in the CpG context were further used for downstream analyses. Samtools and Bedtools were used for interval-related calculation. CG bias was quantified by Picard package. Metagene profiles were calculated by Deeptools.

9. Genome-Wide Hypo-/Hyper-Methylation of cfDNA Analysis

To quantify global DNA hypomethylation and hypermethylation in patients' cfDNA samples, the inventors divided the whole genome into continuous 1-Mb bins and calculated the methylation density of each bin. Methylation density was defined as the number of methylated cytosines divided by the total number of cytosines at CpG context for each bin. The mean and variation of methylation density in healthy samples were calculated and further used to determine whether certain samples were normal by z-score method. Any bins with z-scores larger than 3 or smaller than −3 were considered hypermethylated or hypomethylated and used as potencial features of cancer. RCircos package was used for further genome-wide visualization.

DMRs Analysis

Feature selection of differentially methylated regions (DMRs) for downstream unsupervised clustering was conducted by MethylKit package. DMRs were defined as 1-kb bins with methylation differences larger than 0.4, and q-value smaller than 0.01 between different groups based on logistic regression and SLIM adjustment. Further clustering and PCA analyses were visualized by functions in MethylKit package. Functional annotation was carried out using Homer software, and functional enrichment analyses of all intervals were conducted using GREAT online tool.

11. Plasma DNA Tissue Mapping

The inventors used quadratic programming algorithm for cfDNA methylation profiles deconvolution. WGBS data of 14 tissues from Roadmap project and another two studies were used to find tissue-specific DMRs as reference features. Methylation density for each feature was then calculated in both reference tissues and patient samples. Deconvolution was then performed by R code.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Schwarzenbach, H., Hoon, D.S.B. & Pantel, K. Cell-free nucleic acids as biomarkers in cancer patients. Nature Reviews Cancer 11, 426 (2011).

2. Bettegowda, C. et al. Detection of circulating tumor DNA in early- and late-stage human malignancies. Science translational medicine 6, 224ra224-224ra224 (2014).
3. Alix-Panabières, C. & Pantel, K. Clinical applications of circulating tumor cells and circulating tumor DNA as liquid biopsy. Cancer discovery 6, 479-491 (2016).
4. Murtaza, M. et al. Non-invasive analysis of acquired resistance to cancer therapy by sequencing of plasma DNA. Nature 497, 108 (2013).
5. Chan, K. A. et al. Noninvasive detection of cancer-associated genome-wide hypomethylation and copy number aberrations by plasma DNA bisulfite sequencing. Proceedings of the National Academy of Sciences 110, 18761-18768 (2013).
6. Shaw, J. A. et al. Genomic analysis of circulating cell-free DNA infers breast cancer dormancy. Genome research 22, 220-231 (2012).
7. Klose, R.J. & Bird, A.P. Genomic DNA methylation: the mark and its mediators. Trends in Biochemical Sciences 31, 89-97 (2006).
8. Esteller, M. Epigenetics in cancer. New England Journal of Medicine 358, 1148-1159 (2008).
9. Almouzni, G. & Cedar, H. Maintenance of epigenetic information. Cold Spring Harbor perspectives in biology 8, a019372 (2016).
10. Guo, S. et al. Identification of methylation haplotype blocks aids in deconvolution of heterogeneous tissue samples and tumor tissue-of-origin mapping from plasma DNA. Nature genetics 49, 635 (2017).
11. Wen, L. et al. Genome-scale detection of hypermethylated CpG islands in circulating cell-free DNA of hepatocellular carcinoma patients. Cell research 25, 1250 (2015).
12. Xu, R.-h. et al. Circulating tumour DNA methylation markers for diagnosis and prognosis of hepatocellular carcinoma. Nature Materials 16, 1155 (2017).
13. Kang, S. et al. CancerLocator: non-invasive cancer diagnosis and tissue-of-origin prediction using methylation profiles of cell-free DNA. Genome biology 18, 53 (2017).
14. Feng, H., Jin, P. & Wu, H. Disease prediction by cell-free DNA methylation. Briefings in bioinformatics.
15. Dean, F. B. et al. Comprehensive human genome amplification using multiple displacement amplification. Proceedings of the National Academy of Sciences 99, 5261-5266 (2002).
16. Spits, C. et al. Whole-genome multiple displacement amplification from single cells. Nature protocols 1, 1965 (2006).
17. Lage, J. M. et al. Whole genome analysis of genetic alterations in small DNA samples using hyperbranched strand displacement amplification and array—CGH. Genome research 13, 294-307 (2003).
18. Gawad, C., Koh, W. & Quake, S.R. Single-cell genome sequencing: current state of the science. Nature Reviews Genetics 17, 175 (2016).
19. Chen, C. et al. Single-cell whole-genome analyses by Linear Amplification via Transposon Insertion (LIANTI). Science 356, 189-194 (2017).
20. Olova, N. et al. Comparison of whole-genome bisulfite sequencing library preparation strategies identifies sources of biases affecting DNA methylation data. Genome biology 19, 33 (2018).
21. Fakih, M.G. & Padmanabhan, A. CEA monitoring in colorectal cancer. ONCOLOGY-WILLISTON PARK THEN HUNTINGTON THE MELVILLE NEW YORK-20, 579 (2006).
22. Sun, K. et al. Plasma DNA tissue mapping by genome-wide methylation sequencing for noninvasive prenatal, cancer, and transplantation assessments. Proceedings of the National Academy of Sciences 112, E5503-E5512 (2015).
23. Lun, F. M. et al. Noninvasive prenatal methylomic analysis by genomewide bisulfite sequencing of maternal plasma DNA. Clinical chemistry 59, 1583-1594 (2013).
24. Hodges, E. et al. Directional DNA methylation changes and complex intermediate states accompany lineage specificity in the adult hematopoietic compartment. Molecular cell 44, 17-28 (2011).
25. Smallwood, S. A. et al. Single-cell genome-wide bisulfite sequencing for assessing epigenetic heterogeneity. Nature methods 11, 817-820 (2014).

The invention claimed is:

1. A kit comprising a DNA adaptor comprising a RNA promoter, wherein the cytosines of the RNA promoter are bisulfite-protected.

2. The kit of claim 1, further comprising a ligase and/or ligase buffer.

3. The kit of claim 1 further comprising bisulfite.

4. The kit of claim 1 further comprising a primer that is complementary to the adaptor.

5. The kit of claim 1 further comprising dNTPs.

6. The kit of claim 1 further comprising a DNA polymerase.

7. The kit of claim 1 further comprising nuclease-free water.

8. The kit of claim 1 further comprising a protease.

9. The kit of claim 1 further comprising a RNA polymerase and/or reverse transcriptase.

10. The kit of claim 1 further comprising NTPs.

11. The kit of claim 1 further comprising an oxidant.

12. The kit of claim 1 further comprising a dioxygenase.

13. The kit of claim 1 further comprising a compound comprising a hydroxylamine group, a hydrazine group, or a hydrazide group.

14. The kit of claim 1 further comprising a compound comprising an amine group.

15. The kit of claim 1 further comprising a 3' end-blocked molecule.

16. The kit of claim 1 further comprising SPRI beads.

17. The kit of claim 1 further comprising glucose or modified glucose.

18. The kit of claim 1 further comprising (3-glucosyl-transferase.

* * * * *

UNITED STATES PATENT AND TRADEMARK OFFICE
CERTIFICATE OF CORRECTION

Page 1 of 1

PATENT NO. : 11,905,555 B2
APPLICATION NO. : 18/057424
DATED : February 20, 2024
INVENTOR(S) : Chuan He, Ji Nie and Xiao-Long Cui It is certified that error appears in the above-identified patent and that said Letters Patent is hereby corrected as shown below:

In the Claims

In Claim 18, Column 42, Line 44, please replace "(3-glucosyl-transferase" with --β-glucosyltransferase-- therefore.

Signed and Sealed this
Eighth Day of October, 2024

Katherine Kelly Vidal
*Director of the United States Patent and Trademark Office*

SEQUENCE LISTING

```
Sequence total quantity: 5
SEQ ID NO: 1            moltype = DNA  length = 17
FEATURE                 Location/Qualifiers
source                  1..17
                        mol_type = other DNA
                        organism = synthetic construct
SEQUENCE: 1
taatacgact cactata                                                  17

SEQ ID NO: 2            moltype = AA  length = 375
FEATURE                 Location/Qualifiers
REGION                  1..375
                        note = Description of Artificial Sequence: Synthetic
                        polypeptide
source                  1..375
                        mol_type = protein
                        organism = synthetic construct
SEQUENCE: 2
SHHHHHHSSG VDLGTENLYF QSNAMKIAII NMGNNVINFK TVPSSETIYL FKVISEMGLN   60
VDIISLKNGV YTKSFDEVDV NDYDRLIVVN SSINFFGGKP NLAILSAQKF MAKYKSKIYY  120
LFTDIRLPFS QSWPNVKNRP WAYLYTEEEL LIKSPIKVIS QGINLDIAKA AHKKVDNVIE  180
FEYFPIEQYK IHMNDFQLSK PTKKTLDVIY GGSFRSGQRE SKMVEFLFDT GLNIEFFGNA  240
REKQFKNPKY PWTKAPVFTG KIPMNMVSEK NSQAIAALII GDKNYNDNFI TLRVWETMAS  300
DAVMLIDEEF DTKHRIINDA RFYVNNRAEL IDRVNELKHS DVLRKEMLSI QHDILNKTRA  360
KKAEWQDAFK KAIDL                                                  375
```

```
SEQ ID NO: 3                moltype = DNA   length = 33
FEATURE                     Location/Qualifiers
misc_feature                1..33
                            note = Description of Artificial Sequence: Synthetic primer
source                      1..33
                            mol_type = other DNA
                            organism = synthetic construct
SEQUENCE: 3
agccccgcga aattaatacg actcactata ggg                                           33

SEQ ID NO: 4                moltype = DNA   length = 33
FEATURE                     Location/Qualifiers
misc_feature                1..33
                            note = Description of Artificial Sequence: Synthetic
                              oligonucleotide
source                      1..33
                            mol_type = other DNA
                            organism = synthetic construct
SEQUENCE: 4
ccctatagtg agtcgtatta atttcgcggg gct                                           33

SEQ ID NO: 5                moltype = DNA   length = 16
FEATURE                     Location/Qualifiers
misc_feature                1..16
                            note = Description of Artificial Sequence: Synthetic
                              oligonucleotide
source                      1..16
                            mol_type = other DNA
                            organism = synthetic construct
SEQUENCE: 5
cgactcacta tagggt                                                              16
```